United States Patent [19]

Boyan et al.

[11] Patent Number: 5,656,450
[45] Date of Patent: Aug. 12, 1997

[54] ACTIVATION OF LATENT TRANSFORMING GROWTH FACTOR β BY MATRIX VESICLES

[75] Inventors: Barbara D. Boyan; Zvi Schwartz; Lynda F. Bonewald, all of San Antonio, Tex.

[73] Assignee: Board of Regents, the University of Texas System, Austin, Tex.

[21] Appl. No.: 250,695

[22] Filed: May 27, 1994

[51] Int. Cl.$^6$ .................... C12P 21/06; C12N 11/04; C12N 5/00; A61F 13/00
[52] U.S. Cl. .................. 435/68.1; 424/422; 424/93.7; 424/548; 435/177; 435/180; 435/182; 435/173.1; 435/173.8; 435/325; 435/395; 514/21; 530/812; 530/815; 530/817
[58] Field of Search ........................ 435/68.1, 174, 435/177, 180, 182, 173.1, 173.8, 240.2, 240.21, 240.23, 240.24; 424/422, 93.7, 548; 623/10, 16, 18; 530/840, 812, 815, 817; 514/21

[56] References Cited

U.S. PATENT DOCUMENTS

| | | | |
|---|---|---|---|
| 4,963,489 | 10/1990 | Naughton et al. | 435/240.1 |
| 5,032,508 | 7/1991 | Naughton et al. | 435/32 |
| 5,041,138 | 8/1991 | Vacanti et al. | 623/16 |
| 5,160,490 | 11/1992 | Naughton et al. | 435/284 |

FOREIGN PATENT DOCUMENTS

| | | |
|---|---|---|
| WO/9315114 | 1/1993 | WIPO. |
| WO/9315694 | 8/1993 | WIPO. |

OTHER PUBLICATIONS

Anderson, H.C., "Vesicles Associated with Calcification in the Matrix of Epiphyseal Cartilage," *J. Cell Biol.* (1969) 41:59–72.

Athanasiou, K.A. et al., "The Use of Biodegradable Implants for Repairing Large Articular Cartilage Defects in the Rabbit," *Trans. Orth. Res. Soc.* (1992) 17(1):172.

Bonewald, L.F. et al., "Effects of Combining Transforming Growth Factor β and 1,25-Dihydroxyvitamin $D_3$ on Differentiation of a Human Osteosarcoma (MG-63)," *J. Biol. Chem.* (1992) 267:8943–8949.

Bonewald, L.F. et al., "Stimulation of matrix vesicle enzyme activity inn osteoblast–like cells by 1,25-$(OH)_2D_3$ and transforming growth factor beta (TGF beta)," *Bone Miner.* (1992) 17:139–144.

Bonewald, L.F. et al., "Latent Forms of Transforming Growth Factor–β (TGFβ) Derived from Bone Cultures: Identification of a Naturally Occuring 100–kDa Complex with Similarity to Recombinant Latent TGFβ," *Mol. Endocrinol.* (1991) 5:741–751.

Bonewald, L.F. et al., "Stimulation of Plasma Membrane and Matrix Vesicle Enzyme Activity by Transforming Growth Factor–β in Osteosarcoma Cell Cultures," *J. Cell Physiol.* (1990) 145:200–206.

Boskey, A.L., "Current concepts of the physiology and biochemistry of calcification," *Clin Orthop.* (1981) 157:225–257.

Boskey, A.L. et al., "Studies of matrix–vesicle–induced mineralization in a gelatin gel," *Bone Miner.* (1992) 17:257–262.

Bovan, B.D. et al., "Cell maturation–specific autocrine/paracrine regulation of matrix vesicles," *Bone Miner.* (May 1992) 17(2):263–268.

Boyan, B.D. et al., "In vitro Studies on the Regulation of Endochondral Ossification by Vitamin D," *Crit. Rev. Oral Biol. Med.* (1992) 3(½):15–30.

Boyan, B. D. et al., "Matrix Vesicles as a Marker of Endochondral Ossification," *Connect. Tissue Res.* (1990) 24:67–75.

Boyan, B.D. et al., "Epithelial Cell Lines That Induce Bone Formation in vivo Produce Alkaline Phosphatase–Enriched Matrix Vesicles in Culture," *Clin. Orthop.* (Apr. 1992) 266–276.

Boyan, B.D. et al., "Role of Lipids in Calcification of Cartilage," *Anat. Rec.* (Jun. 1989) 224(2):211–219.

Boyan, B. et al., "Regulation of Matrix Vesicle Metabolism by Vitam D Metabolites," *Connect. Tissue Res.* (1989) 22:3–16.

Boyan, B.D. et al., "Localization of 1,25-$((H)_2D_3$–responsive Alkaline Phosphatase in Osteoblast–like Cells (ROS 17/2.8, MG 63 and MC 3T3) and Growth Cartilage Cells in Culture," *J. Biol. Chem.* (1989) 264(20):11879–11886.

Boyan, B.D. et al., "The Effects of Vitamin D Metabolites on the Plasma and Matrix Vesicle membranes of Growth and Resting Cartilage Cells in vitro," *Endocrinology* (1988) 122:2851–2860.

Boyan, B.D. et al., "Differential Expression of Phenotype by Resting Zone and Growth Region Costochondral Chondrocytes In Vitro," *Bone* (1988) 9:185–194.

Bretaudiere, J.P. and Spillman, T., "Alkaline Phosphatases," In: *Methods of Enzymatic Analysis*, Bergmeyer, H.U. (ed.), Verlag Chemica, Weinheim, Germany (1984) 4:75–93.

Brighton, C.T. and Hunt, R.M., "Mitochondrial Calcium and Its Role in Calcification," *Clin. Orth. Rel Res.* (1974) 100:406–416.

(List continued on next page.)

*Primary Examiner*—David M. Naff
*Attorney, Agent, or Firm*—Greenlee, Winner and Sullivan, P.C.

[57] ABSTRACT

A latent growth factor such as transforming growth factor beta (TGFβ) is converted to active form by matrix vesicles or an extract from matrix vesicles. The matrix vesicles may be stimulated with a Regulator of Enhancing Factor (REF) such as 1,25-dihydroxy vitamin D (1,25-$(OH)_2D_3$) or steroid hormones which may be intercalated into the vesicle membrane. The latent growth factor may be activated in culturing cells such as chondrocytes that have been pretreated with 24,25-$(OH)_2D_3$ to activate cell differentiation, or in healing of bone or cartilage defects, and activation can be carried out in vivo or in vitro. Biodegradable polymeric implants may be prepared containing latent growth factor, REF, matrix vesicle or matrix vesicle extract.

9 Claims, 3 Drawing Sheets

OTHER PUBLICATIONS

Canterbury, J.M. et al., "Metabolic Consequences of Oral Administration of 24,25 Hydroxycholecalciferol to Uremic Dogs," *J. Clin. Invest.* (1980) 65:571–576.

Chomczynski, P. and Sacchi, N., "Single-Step Method of RNA Isolation by Acid Guanidinium Thiocyanate-Phenol-Chloroform Extraction," *Anal. Biochem.* (1987) 162:156–159.

Crabb, L.D., et al., "Synergistic Effect of Transforming Growth Factor–β and Fibroblast Growth Factor on DNA Synthesis in Chick Growth Plate Chondrocytes," *J. Bone Min. Res.* (1990) 5:1105–1112.

Dallas, S.L. et al., "Characterization and Autoregulation of Latent Transforming Growth Factor β (TGFβ) complexes in Osteoblast-like Cell Lines," *J. Biol. Chem.* (1994) 269:6815–6822.

Danielpour et al., "Immunodetection and Quantitation of the Two Forms of Transforming Growth Factor–Beta (TGF–β1 and TGF–β2) Secreted by Cells in Culture," *J. Cell. Physiol.* (1989) 138:79–86.

Davies, L.G. et al., "Formaldehyde Gel for Electrophoretic Separation of RNA and Northern Blot," In: *Basic Methods in Molecular Biology*, Elsevier, New York, N.Y. (1977) 143–149.

Dean, D.D. et al., "Matrix Vesicles Are Enriched in Metalloproteinases That Degrade Proteoglycans," *Calcif. Tissue Int.* (1992) 50:342–349.

Dean, D.D. et al., "Matrix vesicles contain metaloproteinases that degrade proteoglycans," *Bone Miner.* (1992) 17:172–176.

Ecarot–Charrier, B. et al., "Mineralization in Osteoblast Cultures: A Light and Electron Microscopic Study," *Bone* (1988) 9:147–154.

Einhorn, T.A. et al., "Neutral Protein–Degrading Enzymes in Experimental Fracture Callus: A Preliminary Report," *J. Orthrop. Res.* (1989) 7:792–805.

Feinberg, A.P. and Vogelstein, B., "A Technique for Radiolabeling DNA Restriction Endonuclease Fragments to High Specific Activity," *Anal. Biochem.* (1983) 132:6–13.

Fourney, R.M. et al., *Bethesda Res. Lab, Inc. Focus* (1988) 10:5–7.

Gelb, D.E. et al., "The Production of Transforming Growth Factor–β by Chick Growth Plate Chondrocytes in Short Term Monolayer Culture," *Endocrinology* (1990) 127(4):1941–1947.

Gentry, L.E. et al., "Type 1 Transforming Growth Factor Beta: Amplified Expression and Secretion of Mature and Precursor Polypeptides in Chinese Hamster Ovary Cells," *Mol. Cell. Biol.* (1987) 7:3418–3427.

Ginsburg, L. et al., "Synergism Among Oxidants, Proteinases, Phospholipases, Microbial Hemolysins, Cationic Proteins, and Cytokines," *Inflammation* (1992) 16:519–538.

Grigoriadis, A.E. et al., "Effects of Dexamethasone and Vitamin $D_3$ on Cartilage Differentiation in a Clonal Chondrogenic Cell Population," *Endocrinology* (1989) 125:2103–2110.

Hale, L.V. et al., "Effect of Vitamin D Metabolites on the Expression of Alkaline Phosphatase Activity by Epiphyseal Hypertrophic Chondrocytes in Primary Cell Culture," *J. Bone Min. Res.* (1986) 1:489–495.

Hirschman, A. et al., "Neutral Peptidase Activities in Matrix Vesicles from Bovine Fetal Alveolar Bone and Dos Osteosarcoma," *Calcif. Tissue Int.* (1983) 35:791–797.

Howell, D.S. and Dean, D.D., "The Biology, Chemistry and Biochemistry of the Mammalian Growth Plate," In: *Disorders of Bone and Mineral Metabolism*, Coe, F.L. and Favus, M.J. (eds.), Raven Press Ltd., N.Y. (1992) 313–353.

Jingushi, S. et al., "Distribution of acidic fibroblast growth factor, basic fibroblast growth factor, and transforming growth factor β1 in rat growth plate," *Calcium Regulation and Bone Metabolism*, Cohn, D.V., Glorieux, F.H., and Martin, T.J. (eds.), Elsevier Science Publishers (Biomedical Division) New York (1990) vol. 10, 298–303.

Kanzaki, T. et al., "TGF–β1 Binding Protein: A Component of the Large Latent Complex of TGF–β1 with Multiple Repeat Sequences," *Cell* (1990) 61:1051–1061.

Kinoshita, A., et al., "Demonstration of Receptors for Epidermal Growth Factor on Cultured Rabbit Chondrocytes and Regulation of Their Expression by Various Growth and Differentiation Factors," *Biochem. Biophys. Res. Comm.* (1992) 183:14–20.

Langston, G.G. et al., "Effect of 1,25–$(OH)_2D_3$ and 24,25–$(OH)_2D_3$ on *Calcium Influxes in Costochondral Chondrocyte Cultures*," *Calcif. Tissue Int.* (1990) 47:230–236 [or 47: ?].

Lehrach, H. et al., "RNA Molecular Weight Determinations by Gel Electrophoresis under Denaturing Conditions, a Critical Reexamination," *Biochemistry* (1977) 16:4743–4751.

Liberherr, M. et al., "Interaction of 24,25–Dihydroxyvitamin $D_3$ and Parathyroid Hormone on Bone Enzymes in Vitro," *Calcif. Tissue Int.* (1979) 27:47–52.

Lowry, O.H. et al., "Protein Measurement with the Folin Phenol Reagent," *J. Biol. Chem.* (1951) 193:265–275.

Madisen, L. et al., "High–Level Expression of TGF–β2(414) Precursor in Chinese Hamster Ovary Cells," *Growth Factors* (1990) 3:129–138.

Miyazono, K. et al., "Latent High Molecular Weight Complex of Transforming Growth Factor β1," *J. Biol. Chem.* (1988) 263(13):6407–6415.

Mow, V.C. et al., "Biphasic Creep and Stress Relaxation of Articular Cartilage in Compression: Theory and Experiments," *J. Biomech. Eng.* (1980) 102:73–83.

Nasatzky, E. et al., "Sex–Dependent Effects of 17–Beta–Estradiol on Chondrocyte Differentiation in Culture," *J. Cell Physiol.* (1993) 154:359–367.

Norman, A.W. "1,25–Dihydroxyvitamin $D_3$ and 24,25–Dihydroxyvitamin $D_3$: Key Components of the Vitamin D Endocrine System," *Contr. Nephrol.* (1980) 18:1–11.

O'Keefe, R.J. et al., "TGF–β, Basic FGF, and IGF–1 Demonstrate Interactive and Synergistic Effects on DNA Synthesis in Growth Plate Condrocytes," *Bone Min. Res.* (1988) 3:S176.

O'Keefe, R.J. et al., "Articular and Growth Plate Chondrocytes Exhibit Markedly Different Metabolic Responses to Growth Factors," *Bone Min. Res.* (1988) 3:S185.

O'Keefe, R.J. et al., "Effects of Transforming Growth Factor β on Matrix Synthesis by Chick Growth Plate Chondrocytes," *Endocrinology* (1988) 122(6):2953–2961.

Oreffo, R.O.C. et al., "Activation of the Bone–Derived Latent TGF Beta Complex by Isolated Osteoclasts," *Biochem. Biophys. Res. Comm.* (1989) 158(3):817–823.

Ornoy, A. et al., "24,25–Dihydroxyvitamin $D_3$ is a metabolite of vitamin D essential for bone formation," *Nature* (1978) 276:517–520.

Oursler, M.J., "Osteoclast Synthesis and Secretion and Activation of Latent Transforming Growth Factor β," *J. Bone Min. Res.* (1994) 9(4):443–452.

Peterkofsky, B. and Diegelmann, R., "Use of a Mixture of Proteinase–Free Collagenases for the Specific Assay of Radioactive Collagen in the Presence of Other Proteins," *Biochemistry* (1971) 10(6):988–994.

Raisz, L.G. and Kream, B.E., "Regulation of Bone Formation," (First of Two Parts), *N. Eng. J. Med.* (1983) 309:29–35.

Raisz, L.G. and Kream, B.E., "Regulation of Bone Formation," (Second of Two Parts), *N. Eng. J. Med.* (1983) 309:83–89.

Raisz, L.G. et al., "Comparison of the Effects of a Potent Synthetic Analog of Bovine Parathyroid Hormone with Native bPTH–(1–84) and Synthetic bPTH–(1–34) on Bone Resorption and Collagen Synthesis," *Calcif. Tissue Int.* (1979) 29:215–218.

Rosier, R.N. et al., "Transforming Growth Factor Beta: An Autocrine Regulator of Chondrocytes," *Connect. Tissue Res.* (1989) 20:295–301.

Saito, S. et al., "Transforming growth factor–beta (TGF–$\beta$) in human milk," *Clin. Exp. Immunol.* (1993) 94:220–224.

Sato, Y. and Rifkin, D.B., "Inhibition of Endothelial Cell Movement by Pericytes and Smooth Muscle Cells: Activation of a Latent Transforming Growth Factor–$\beta$1–like Molecule by Plasmin during Co–culture," *J. Cell Biol.* (1989) 109:309–315.

Schmitz, J. et al., "Characterization of Rat Calvarial Non-union Defects," *Acta Anatomica* (1990) 138:185–192.

Schwartz, Z. et al., "Gender–Specific, Maturation–Dependent Effects of Testosterone on Chondrocytes in Culture," *Endocrinology* (1994) 134(4):1640–1647.

Schwartz, Z. et al., "Direct Effects of Transforming Growth Factor–$\beta$ on Chondrocytes Are Modulated by Vitamin D Metabolites in a Cell Maturation–Specific Manner," *Endocrinology* (1993) 132:1544–1552.

Schwartz, Z. et al., "Production of 1,25–Dihydroxyvitamin $D_3$ and 24,25–Dihydroxyvitamin $D_3$ by Growth Zone and Resting Zone Chondrocytes Is Dependent on Cell Maturation and Is Regulated by Hormones and Growth Factors," *Endocrinology* (1993) 130(5):2495–2504.

Schwartz, Z. et al., "In vivo regulation of matrix vesicle concentration and enzyme activity during primary bone formation," *Bone Miner.* (1992) 17:134–138.

Schwartz, Z. et al., "Differential Regulation of Prostaglandin E2 Synthesis and Phospholipase $A_2$ Activity by 1,25–$(OH)_2D_3$ in Three Osteoblast–like Cell Lines (MC–3T3–E1, ROS 17/2.8 and MG–63)," *Bone* (1992) 13:51–58.

Schwartz, Z. et al., "Regulation of Prostaglandin $E_2$ Synthesis by Vitamin D Metabolites in Growth Zone and Resting Zone Chondrocyte Cultures is Dependent on Cell Maturation," *Bone* (1992) 13:395–401.

Schwartz, Z. et al., "Modulation of Matrix Vesicle Enzyme Activity and Phosphatidylserine Content by Ceramic Implant Materials during Endosteal Bone Healing," *Calcif. Tissue* (1992) 51:429–437.

Schwartz, Z. et al., "Inhibition of 1,25–$(OH)_2D_3$ and 24,25–$(OH)_2D_3$–Dependent Stimulation of Alkaline Phosphatase Activity by A23187 Suggests a Role for Calcium in the Mechanism of Vitamin D Regulation of Chondrocyte Cultures," *J. Bone Min. Res.* (1991) 6:709–718.

Schwartz, Z. et al., "Effects of hydroxyapatite implants on primary mineralization during rat fibial healing: biochemical and morphometric analysis," *J. Biomed. Mater. Res.* (1993) 27:1029–1038.

Schwartz, Z. et al., "Effect of Glass Ceramic and Titanium Implants on Primary Calcification During Rat Tibial Bone Healing," *Calcif. Tissue Int.* (1991) 49:359–364.

Schwartz, Z. et al., "A Direct Effect of 24,25–$(OH)_2D_3$ and 1,25–$(OH)_2D_3$ on the Modeling of Fetal Mice Long Bones In Vitro," *J. Bone Min. Res.* (1989) 4(2):157–163.

Schwartz, Z. et al., "Changes in Extracellular Matrix Vesicles during Healing of Rat Tibial Bone: A Morphometric and Biochemical Study," *Bone* (1989) 10:53–60.

Schwartz, Z. et al., "Direct Effects of 1,25–Dihydroxyvitamin $D_3$ and 24,25–Dihydroxyvitamin $D_3$ on Growth Zone and Resting Zone Chondrocyte Membrane Alkaline Phosphatase and Phospholipase–$A_2$ Specific Activities," *Endocrinology* (1988) 123(6):2878–2884.

Schwartz, Z. and Boyan, B., "The Effects of Vitamin D Metabolites on Phospholipase $A_2$ Activity of Growth Zone and Resting Zone Cartilage Cells in Vitro," *Endocrinology* (1988) 122:2191–2198.

Schwartz, Z. et al., "Localization of Vitamin $D_3$ responsive Alkaline Phosphatase in Cultured Chondrocytes," *J. Biol. Chem.* (1988) 263:6023–6026.

Seyedin, S.M. et al., "Cartilage–inducing Factor–B is a Unique Protein Structurally and Functionally Related to Transforming Growth Factor–$\beta$," *J. Biol. Chem.* (1987) 22;1946–1949.

Seyedin, S.M. et al, "Cartilage–inducing Factor–A," *J. Biol. Chem.* (1986) 261(13):5693–5695.

Seyedin, S.M. et al., "Purification and characterization of two cartilage–inducing factors from bovine demineralized bone," *Proc. Natl. Acad. Sci. USA* (1985) 82:2267–2271.

Spilker et al., "Effects of Friction on the Unconfined Compressive Response of Articular Cartilage: A Finite Element Analysis," *J. Biomech. Eng.* (1990) 112:138–146.

Suzuki, F., "Effects of Various Growth Factors on a Chondrocyte Differentiation Model," *Prostate Cancer and Bone Metastasis*, (J.P. Karr and H. Yamanaka Eds.) Plenum Press, New York (1992) 324:101–106.

Swain, L.D. et al., "Nongenomic Regulation of Chondrocyte Membrane Fluidity by 1,25–$(OH)_2D_3$ and 24,25–$(OH)_2D_3$ Is Dependent on Cell Maturation," *Bone* (1993) 14:609–617.

Swain, L. et al., "1,25–$(OH)_2D_3$ and 24,25–$(OH)_2D_3$ regulation of arachidonic acid turnover in chondrocyte cultures is cell maturation–specific and may involve direct effects on phospholipase $A_2$," *Biochim. Biophys. Acta* (1992) 1136:45–51.

Swain, L.D. et al., "Regulation of matrix vesicle phospholipid metabolism is cell maturation–dependent," *Bone Miner.* (1992) 17:192–196.

Sylvia, V.L. et al., "Maturation–Dependent Regulation of Protein Kinase C Activity by Vitamin $D_3$ Metabolites in Chondrocyte Cultures," *J. Cell. Physiol.* (1993) 157:271–278.

Thorp, B.H. et al., "Transforming Growth Factor–$\beta$1, –$\beta$2 and –$\beta$3 in cartilage and bone cells during endochondral ossification in the chick," *Development* (1992) 114:907–911.

Tsuji, T. et al., "Moleculr cloning of the large subunit of transforming growth factor type $\beta$ masking protein and expression of the mRNA in various rat tissues," *Proc. Natl. Acad. Sci. USA* (1990) 87:8835–8839.

Twardzik, D.R. et al., "$\gamma$–Interferon–Induced Activation of Latent Transforming Growth Factor–$\beta$ by Human Monocytes," *Ann. N.Y. Acad. Sci.* (1990) 593:276–284.

Wakefield, L.M. et al., "Latent Transforming Growth Factor–β from Human Platelets," *J. Biol. Chem.* (1988) 263:7646–7654.

Wegedahl, J.E. et al., "Differentiation of Normal Human Bone Cells by Transforming Growth Factor–β and 1,25(OH)$_2$ Vitamin D$_3$," *Metabolism* (1992) 41(1):42–48.

Yang, F. et al., "α$_2$–HS–glycoprotein: Expression in Chondrocytes and Augmentation of Alkaline Phosphatase and Phospholipase A2 Activity," *Bone* (1991) 12:7–15.

Beresford, J.N. et al., "1,25–Dihydroxyvitamin D$_3$ and Human Bone–Derived Cells in Vitro: Effects on Alkaline Phosphatase, Type I Collagen and Proliferation," *Endocrinology* (1986) 119(4):1776–1785.

Schwartz, Z. and Boyan, B.D. "Underlying Mechanisms at the Bone–Biomaterial Interface," *J. Cellular Biochemistry* (1994) 56:340–347.

Schwartz, Z. et al., "Regulation of arachidonic acid turnover by 1,25–(OH)$_2$D$_3$ and 24,25–(OH)$_2$D$_3$ in growth zone and resting zone chondrocyte cultures," *Biochimica et Biophysica Acta* (1990) 1027:278–286.

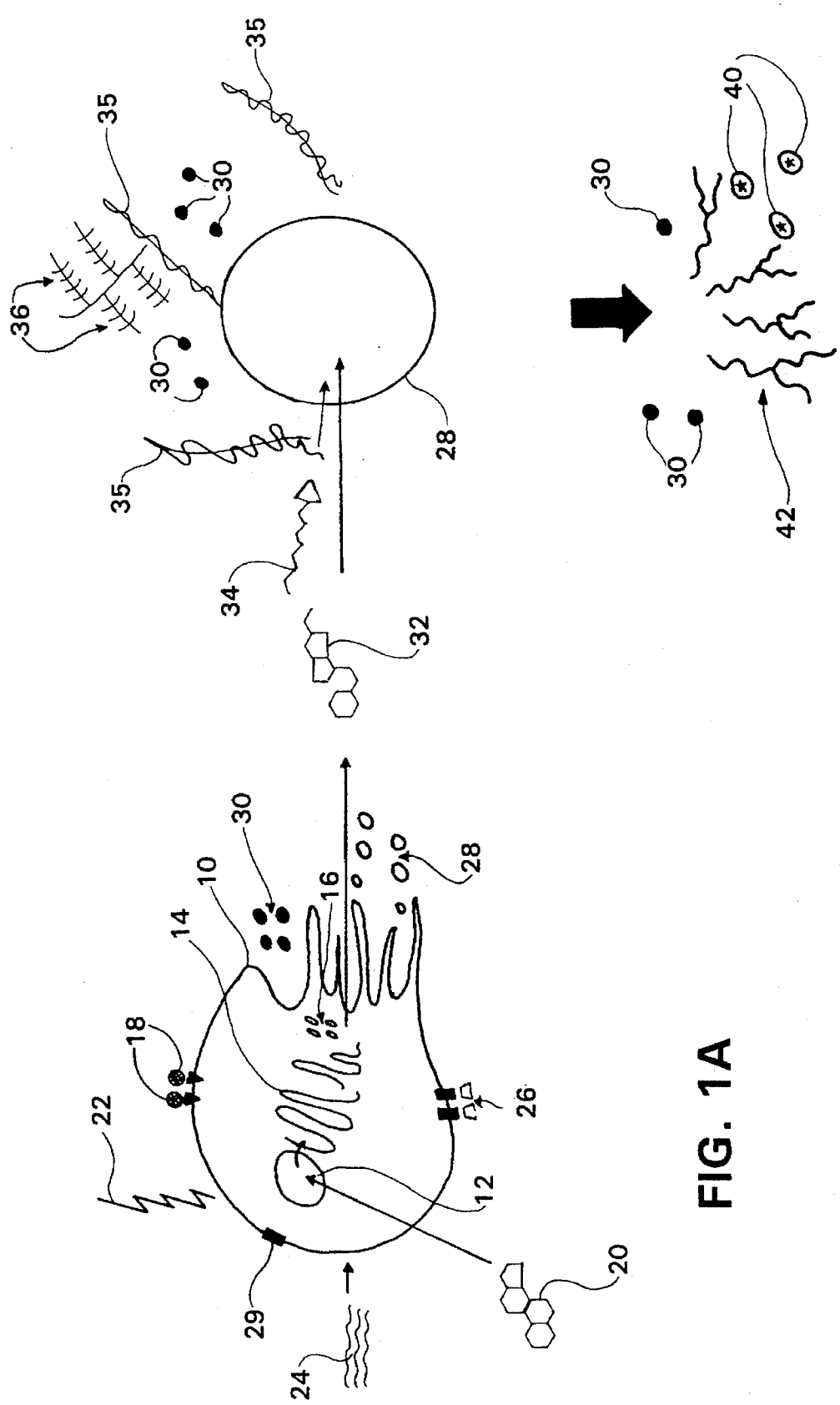

ACTIVATION OF LATENT TRANSFORMING GROWTH FACTOR β BY MATRIX VESICLES

The United States Government owns rights in the present invention pursuant to Public Health Service grants DE 05937, DE 08603, P01 R8 39529, and AR 39357.

FIELD OF THE INVENTION

This invention lies in the field of compositions and methods for effecting wound healing, specifically, the activation of latent growth factor through matrix vesicles by stimulation with Regulator of Enhancing Factor (REF).

BACKGROUND OF THE INVENTION

Endochondral bone formation consists of a developmental cascade of cellular differentiation that culminates in extracellular matrix mineralization. The process is required for normal growth and development of long bones and for certain kinds of bone repair. During the chondrogenic phase of the process, chondrocytes are responsible for the synthesis, maintenance and maturation of a calcifiable extracellular matrix that is composed mainly of proteoglycan and collagen. (Boskey, A. L. (1991), "Current concepts of the physiology and biochemistry of calcification," Clin. Orthop. 157:225–257; Howell, D. S. and Dean, D. D. (1992), "Biology, chemistry and biochemistry of the mammalian growth plate," In: Disorders of Bone and Mineral Metabolism, Coe, F. L. and Favus, M. J. (eds), Raven Press Ltd., New York 313–353.)

The complex regulation of chondrocyte differentiation by growth factors such as TGFβ and other hormones has been shown by numerous investigators. (Crabb, I. D., et al. (1990), "Synergistic effect of transforming growth factor-β and fibroblast growth factor on DNA synthesis in chick growth plate chondrocytes," J. Bone Min. Res. 5:1105–1112; Kinoshita, A., et al. (1992), "Demonstration of receptors for epidermal growth factor on cultured rabbit chondrocytes and regulation of their expression by various growth and differentiation factors," Biochem. Biophys. Res. Comm. 183:14–20; Suzuki, F. (1992), "Effects of various growth factors on a chondrocyte differentiation model," Adv. Exper. Med. and Biol. 324:101–106; Thorp, B. H., et al. (1992), "Transforming growth factor-β1, -β2, and -β3 in cartilage and bone cells during endochondral ossification in the chick," Development 114:907–911).

Vitamin $D_3$ is known to be an essential regulator of this complex process, and both 1,25-$(OH)_2D_3$ and 24,25-$(OH)_2D_3$ are involved. (Raisz, L. G. and Kream, B. E. (1983), "Regulation of bone formation," (first of two parts), N. Engl. J. Med. 309:29–35; Raisz, L. G. and Kream, B. E. (1983), "Regulation of bone formation," (second of two parts), N. Engl. J. Med. 309:83–89; Canterbury, J. M., et al. (1980), "Metabolic Consequences of oral administration of 24,25 hydroxycholecalciferol to uremic dogs," J. Clin. Invest. 65:571–580; Liberherr, M. et al. (1979), "Interaction of 24,25-dihydroxyvitamin $D_3$ and parathyroid hormone on bone enzymes in vitro," Calcif. Tissue Int. 27:47–53; Ornoy, A., et al. (1978), "24,25-Dihydroxyvitamin $D_3$ is a metabolite of vitamin D essential for bone formation," Nature 276:517–520; and Norman, A. W. (1980), "1,25-Dihydroxyvitamin $D_3$ and 24,25-dihydroxyvitamin $D_3$: key components of the vitamin D endocrine system. Contr. Nephrol. 18:1–11; Grigoriadis, A. E., et al. (1989), "Effects of dexamethasone and vitamin $D_3$ on cartilage differentiation in a clonal chondrogenic cell population," Endocrinology 125:2103–2110; Schwartz, Z., et al. (1992), "Direct effects of transforming growth factor β on chondrocytes are modulated by vitamin D metabolites in a cell maturation specific manner," Endocrinology 132:1544–1552; Schwartz, Z. et al., "Differential Regulation of prostaglandin E2 synthesis and phospholipase $A_2$ activity by 1,25-$(OH)_2D_3$ in three osteoblast-like cell lines (MC-373-E1), ROS 17/2.8 and MG-63", Bone (1992) 13:51–58.)

Matrix vesicles, and the phospholipids present in them, are involved in initial formation of calcium hydroxyapatite crystals via the interaction of calcium and phosphate ions with phosphatidylserine to form phospholipid:Ca:Pi complexes (CPLX). CPLX is present in tissues which are undergoing initial mineral deposition but are absent from nonmineralizing tissues. Evidence suggests that CPLX resides in the interior of matrix vesicles where the earliest mineral crystals are formed in association with the vesicle membrane. More recently, it has been determined that specific membrane proteins, called proteolipids, participate in CPLX formation and hydroxyapatite deposition, in part by structuring phosphatidylserine in an appropriate conformation. Phosphatidylserine involvement in the initiation of mineralization has been extensively investigated because of its extremely high binding affinity for $Ca_{2+}$. In addition to structuring a specific phospholipid environment, proteolipids may also act as ionophores, promoting export of protons and import of calcium and phosphate, both requirements of biologic calcification (Boyan, B. D. et al., "Role of lipids in calcification of cartilage," Anat. Rec. (June 1989) 224(2):211–219).

There is a known correlation between in vivo bone formation and in vitro production of normal matrix vesicles (Boyan, B. D. et al., "Epithelial cell lines that induce bone formation in vivo produce alkaline phosphatase-enriched matrix vesicles in culture," Clin. Orthop. (April 1992) 266–276).

Many cells produce growth factors in latent form and store them in their extracellular matrix, or they may store them in an inactive form via specific binding proteins. These growth factors may be activated at a later time and act on the original cell as autocrine factors, or a neighboring cell as paracrine factors, or they may be released into the circulation and have a systemic effect as endocrine agents. One function of the extracellular matrix vesicles is to transport enzymes for matrix modification (Boskey, A. L. et al., "Studies of matrix-vesicle-induced mineralization in a gelatin gel," Bone Miner. 17:257–262). Matrix vesicles are selectively enriched in enzymes that degrade proteoglycans (Dean, D. D. et al., "Matrix vesicles contain metaloproteinases that degrade proteoglycans," Bone Miner. (1992) 17:172–176).

Transforming growth factor beta (TGFβ) is an important regulator of cartilage development and chondrocyte differentiation (Seyedin, S. M., et al., J. Biol. Chem (1987) 262:1946–1949; Seyedin, S. M., et al., Proc. Natl. Acad. Sci. USA (1985) 82:2267–2271; Seyedin, S. M., et al., J. Biol. Chem. (1986) 261:5693–5695). It is synthesized by chondrocytes and appears to act in an autocrine manner (Gelb, D. E., et al., Endocrinology (1990) 127:1941–1947; Schwartz, Z., et al., "Direct effects of transforming growth factor-beta on chondrocytes are modulated by vitamin D metabolites in a cell maturation-specific manner," Endocrinology (1993) 132:1544–1552; Rosier, R. N., et al., Connect. Tissue Res. (1989) 20:295–301). TGFβ production varies with stage of chondrocyte differentiation.

TGFβ is produced by many cell types in a latent form which may be released into the circulation, as during platelet lysis (Wakefield, L. M., et al., J. Biol. Chem. (1988) 263:7646–7654; Miyazono, K., et al., J. Biol. Chem. (1988) 263:6407–6415) or targeted for storage in the extracellular matrix (Dallas, S. L., et al., J. Biol. Chem. (1994) 269:6815–6822). Latent TGFβ exists in a number of macromolecular forms. Recombinant human TGFβ$_1$ is a homodimer of 100 kD which contains a latency-associated peptide non-covalently bound to the mature TGFβ molecule (Gentry, L. E., et al. (1987), Mol. Cell. Biol. 7:3418–3427). Latent TGFβ synthesized by fibroblasts consists of a similar or identical 100 kD homodimer covalently bound through a cysteine residue to a 190 kD TGFβ binding protein (Kanzaki, T., et al. (1990), Cell 61:1051–1061; Tsujmi, T., et al. (1990), Proc. Natl. Acad. Sci. U.S.A. 87:8835–8839). Platelets produce a latent TGFβ that contains a truncated form of the 190 kD binding protein (Wakefield, et al. (1988), J. Biol. Chem. 263:7646–7654). Bone cells produce large amounts of the 100 kD complex (Bonewald, L. et al. (1991), Mol. Endocrinol. 5:741–751) in addition to the fibroblast form of latent TGFβ (Dallas, S. L., et al. (1994), J. Biol. Chem. 269:6815–6822).

Storage of latent TGFβ and the mechanism, as well as timing, of activation of latent TGFβ appears to be specific for each cell and tissue type. A variety of factors may stimulate cells to activate latent TGFβ. For example, macrophages treated with γ-interferon activate latent TGFβ (Twardzik, D. R., et al., Ann. N.Y. Acad. Sci. (1990) 593:276–284), as will osteoclasts treated with retinol (Oreffo, R.O.C., et al., Biochem. Biophys. Res. Comm. (1989) 153:817–823).

Local production of acid may be one mechanism by which latent TGFβ is activated. For example, it is believed that latent TGFβ in milk is activated by stomach acid and that the active form is transported through the gut (Saito, S., et al., Clin. Exp. Immunol. (1993) 94:220–224). While acid pH can activate latent TGFβ, it is clear that proteases play an important role in most systems. Endothelial cells activate latent TGFβ through the plasmin system (Sato, Y. and Rifkin, D. B., J. Cell Biol. (1989) 109:309–315). Arian osteoclasts appear to use multiple proteases in addition to acid pH (Oursler, M. J., J. Bone Min. Res. (1994) 9:443–452). In growth plate cartilage and unmineralized osteoid in bone, where local generation of acid has not been reported, participation of proteases is an attractive option.

Recent studies have shown that proteinases, including neutral and acid metalloproteinases and plasminogen activator, and various peptidases are present at high levels in matrix vesicles (Hirschman, A., et al., Calcif. Tissue Int. (1983) 35:791–797; Einhorn, T. A., et al., J. Orthop. Res. (1989) 7:792–805; Dean, D. D., et al., "Matrix vesicles are enriched in metalloproteinases that degrade proteoglycans," Calcif. Tissue Int. (1992) 50:342– 349). These extracellular organelles are membrane bounded, produced by chondrocytes and osteoblasts in vivo (Anderson, H. C., J. Cell Biol. (1969) 41:59–72; Schwartz, Z., et al., Bone (1989) 10:53–60) and in vitro (Boyan, B. D., et al., "Differential expression of phenotype by resting zone and growth region costochondral chondrocytes in vitro," Bone (1988) 9:185–194; Boyan, B. D., et al., J. Biol. Chem. (1989) 264:11879–11886; Ecarot-Charrier, B., et al., Bone (1988) 9:147–154), are found in the extracellular matrix, and are associated with modification of the extracellular matrix prior to calcification.

Matrix vesicles have a distinctive phospholipid composition and enzyme activity. Their characteristics are cell-maturation dependent. Regulation of matrix vesicle structure and function occurs at the genomic and non-genomic levels.

By following alkaline phosphatase gene transcription, protein concentration, and enzyme specific activity, it has been shown that steroid hormones and growth factors exhibit a regulatory influence over gene transcription, protein synthesis, and matrix vesicle activity. Matrix vesicles respond to peptide hormones such as testosterone (Schwartz, Z., et al. "Gender-specific, maturation-dependent effects of testosterone on chondrocytes in culture," Endocrinology (1994) 134:1640–1647); estrogen (Nasatzky, E., et al., "Sex-dependent effects of 17-beta-estradiol on chondrocyte differentiation in culture," J. Cell Physiol. (1993) 154:359–367); growth factors such as TGFβ (Bonewald, L. F., et al., "Stimulation of plasma membrane and matrix vesicle enzyme activity by transforming growth factor-beta in osteosarcoma cell cultures," J. Cell Physiol (1990) 145:200–206); other matrix proteins, like alpha 2-HS-glycoprotein (Yang, F. et al., "Alpha 2-HS-glycoprotein: expression in chondrocytes and augmentation of alkaline phosphatase and phospholipase A2 activity," Bone (1991) 12:7–15); and autocoid mediators like prostaglandins as well. Calcifying cells can modulate events in the matrix via direct autocrine/paracrine stimulation or inhibition of the matrix vesicles. 1,25-dihydroxy vitamin D$_3$ (1,25-(OH)$_2$D$_3$) and 24,25-dihydroxy vitamin D$_3$ (24,25-(OH)$_2$D$_3$) regulate matrix vesicle phospholipase A$_2$ activity, fatty acid turnover, arachidonic acid release, PGE2 production, and membrane fluidity, which can act on the matrix vesicle to alter enzyme activity (Boyan, B. D., et al., "Cell maturation-specific autocrine/paracrine regulation of matrix vesicles," Bone Miner. (May 1992) 17(2):263–268).

Matrix vesicle structure and function, as well as extracellular matrix synthesis by osteoblasts and chondrocytes, are regulated by TGFβ as well as vitamin D metabolites (Schwartz, Z., et al., Endocrinology (1993) 132:1544–1552; Miyazono, K., et al., J. Biol. Chem. (1988) 263:6407–6415; Bonewald, L., et al., J. Cell Physiol. (1990) 145:200–206; Boyan, B. D., et al., "In vitro studies on the regulation of endochondral ossification by vitamin D," Crit. Rev. Oral Biol. Med. (1992) 3(½):15–30; Schwartz, Z., et al., Endocrinology (1988) 123:2878–2884; Boyan, B. D. et al., "Matrix vesicles as a marker of endochondral ossification," Connect. Tissue Res. (1990) 24:67–75; Bonewald, L. F. et al., "Stimulation of matrix vesicle enzyme activity in osteoblast-like cells by 1,25-(OH)$_2$D$_3$ and transforming growth factor beta (TGF beta)," Bone Miner. (1992) 17:139–144; Swain, L. D. et al., "Regulation of matrix vesicle phospholipid metabolism is cell maturation-dependent," Bone Miner. (1992) 17:192–196). Moreover, it appears that these two regulators interact in a specific manner during cell differentiation. The details of this interaction have been partially elucidated by using chondrocytes derived from costochondral cartilage. Resting zone and growth zone chondrocytes constitutively produce 1,25-(OH)$_2$D$_3$ and 24,25-(OH)$_2$D$_3$, and TGFβ regulates this production (Schwartz, Z., et al., Endocrinology (1993) 132:1544–1552). Vitamin D metabolites alter membrane fluidity (Swain, L. D., et al., "Nongenomic regulation of chondrocyte membrane fluidity by 1,25-(OH)$_2$D$_3$ and 24,25-(OH)$_2$D$_3$ is dependent on cell maturation," Bone (1993) 14:609–617) and enzyme activity (Schwartz, Z. and Boyan, B., Endocrinology (1988) 122:2191–2198) of isolated matrix vesicles in vitro. Nongenomic effects of 1,25-(OH)$_2$D$_3$ and 24,25-(OH)$_2$D$_3$ have been reported and include alterations in arachidonic acid turnover (Schwartz, Z., et al., "Regulation of arachidonic acid turnover by 1,25-(OH)$_2$D$_3$ and 24,25-(OH)$_2$D$_3$ in growth zone and resting zone chondrocyte cultures," Biochim. Biophys. Acta (1990)

102:278–286; Swain, L., et al., Biochim. Biophys. Acta (1992) 1136:45–51; Boyan, B. et al., Connect. Tissue Res. (1989) 22:3–16), calcium ion flux (Langston, G. G., et al., Calcif. Tissue Int. (1990) 17:230–236; Schwartz, Z. et al., "Inhibition of 1,25-$(OH)_2D_3$ and 24,25-$(OH)_2D_3$-dependent stimulation of alkaline phosphatase activity by A23187 suggests a role for calcium in the mechanism of vitamin D regulation of chondrocyte cultures," J. Bone Min. Res. (1991) 6:709–718), and protein kinase C activity (Sylvia, V. L., et al., "Maturation-dependent regulation of protein kinase C activity by vitamin $D_3$ metabolites in chondrocyte cultures," J. Cell Physiol. (1993) 157:271–278).

TGFβ and vitamin D have been shown to synergize with respect to alkaline phosphatase induction in bone cell lines (Bonewald, L. F., et al., Mol. Endocrinol. (1991) 5:741–751; Bonewald, L. F., et al., "Effects of combining transforming growth factor beta and 1,25-dihydroxyvitamin $D_3$ on differentiation of a human osteosarcoma (MG-63)," J. Biol. Chem. (1992) 267:8943–8949), primary human bone cells (Wegedahl, J. E., et al., Metabolism (1992) 41:42–48), and rat resting zone chondrocytes (Schwartz, Z., et al., Endocrinology (1993) 132:1544–1552). Both TGFβ and vitamin D regulate chondrocyte differentiation. Exogenous TGFβ stimulates DNA synthesis and matrix formation in chick growth plate chondrocytes (Rosier, R. N., et al., Calcif. Tissue Res. (1988) 20:295–301; Crabb, I. D., et al., J. Bone Min. Res. (1990) 5:1105–1112; O'Keefe, R., et al., J. Bone Min. Res. (1988) 3:S67). In rat growth plate chondrocytes, rhTGFβ1 regulates alkaline phosphatase, phospholipase $A_2$ (Schwartz, Z., et al., Endocrinology (1993) 132:1544–1552), as well as vitamin D metabolite production (Schwartz, Z., et al., Endocrinology (1992) 130:2495–2504). Cellular response to TGFβ depends on the state of endochondral maturation, with resting zone cells exhibiting a differential response compared to that observed in growth zone cell cultures. Similarly, vitamin D metabolites also regulate the expression of alkaline phosphatase (Schwartz, Z. and Boyan, B., Endocrinology (1988) 122:2191–2198), phospholipase $A_2$, and protein kinase C (Sylvia, V. L., et al., "Maturation-dependent regulation of protein kinase C activity by vitamin $D_3$ metabolites in chondrocyte cultures," J. Cell Physiol. (1993) 157:271–278) in chondrocytes in a cell maturation-specific manner.

Active metalloproteinases are present in matrix vesicles (Hirschman, A., et al., Calcif. Tissue Int. (1983) 35:791–797; Einhorn, T. A., et al., J. Orthop. Res. (1989) 7:792–805; Dean, D. D., et al., Calcif. Tissue Int. (1992) 50:342–349). In growth plate, the immunohistochemical distribution of TGFβ1 (Jingushi, S., et al., *Calcium Regulation and Bone Metabolism*, Cohn, D. V., Glorieux, F. H., and Martin, T. J. (eds.), Elsevier Science Publishers (Biomedical Division) New York, (1990) Vol. 10,298–303) coincides with the localization of matrix vesicles in the territorial matrix of the cells (Anderson, H. C., J. Cell Biol. (1969) 41:59–72). Active acid and neutral metalloproteinases, as well as plasminogen activator, are present in matrix vesicles and require physical destruction of the matrix vesicle membrane for their release (Dean, D. D., et al., Calcif. Tissue Int. (1992) 50:342–349).

Other enzymes present in matrix vesicles are sensitive to regulation by TGFβ and vitamin D metabolites (Schwartz, Z., et al., Endocrinology (1993) 132:1544–1552; Schwartz, Z., et al., Endocrinology (1988) 123:2878–2884; Sylvia, V. L., et al., J. Cell Physiol. (1993) 157:271–278; Boyan, B. D., et al., Endocrinology (1988) 122:2851–2860). In both instances the effects are cell maturation-dependent and vitamin D metabolite-specific. 1,25-$(OH)_2D_3$ stimulates matrix vesicle phospholipase $A_2$ (Schwartz, Z. and Boyan, B., Endocrinology (1988) 122:2191–2198), increasing the production of lyso derivatives, resulting in loss of membrane integrity (Ginsburg, L. et al., Inflammation (1992) 16:519–538). In contrast, 24,25-$(OH)_2D_3$ inhibits matrix vesicle phospholipase $A_2$ (Schwartz, Z. and Boyan, B., Endocrinology (1988) 122:2191–2198), potentially resulting in a more stable membrane and retention of metalloproteinases within the matrix vesicle.

Matrix vesicle membrane fluidity (Swain, L. D., et al., Bone (1993) 14:609–617) and enzyme activity (Schwartz, Z., et al., Endocrinology (1988) 123:2878–2884) can be directly and specifically regulated by 1,25-$(OH)_2D_3$ in the absence of the cell and its molecular and protein synthetic machinery.

Matrix vesicles have been associated with wound healing (Schmitz, J. et al., Acta Anatomica (1990) 138:185–192; Einhorn, T. A. et al., J. Orthop. Res. (1989) 7:792–805; Brighton, C. T. and Hunt, R. M., Clin. Orth. Rel. Res. (1974) 100:406–416), however the role of matrix vesicles in wound healing has not previously been known. Endochondral wound healing is stimulated by application of electrical energy possibly through stimulation of matrix vesicle production by cells. C. T. Brighton and R. M. Hunt noted that stimulation of non-union tissue with electromagnetic fields causes an increase in the number of matrix vesicles as well as in the formation of crystals and calcification of the matrix. This was followed by healing of the nonunion defect with calcified cartilage and bone.

Cartilage and bone wound healing are also aided through placing implants made of bioerodible polymers into the defects. Such bioerodible polymers are described, e.g. in U.S. patent application Ser. No. 08/123,812 filed Sep. 20, 1993, and corresponding PCT publication WO/9315694, published Aug. 19, 1993, and U.S. Pat. No. 08/196,970 filed Feb. 15, 1994, all of which are incorporated herein by reference. Such implants may contain growth factors and other agents for promotion of wound healing.

Bone-bonding implants such as KG Cera, Mina 13, and titanium support an increase in matrix vesicle concentration compared with nonbone-bonding implants (Schwartz, Z. et al., "Effect of glass ceramic and titanium implants on primary calcification during rat fibial bone healing," Calcif. Tissue Int. (1991) 49:359–364) and also lead to increased alkaline phosphatase and phospholipase $A_2$ (Schwartz, Z. et al., "In vivo regulation of matrix vesicle concentration and enzyme activity during primary bone formation," Bone Miner. (1992) 17:134–138; Schwartz, Z. et al., "Modulation of matrix vesicle enzyme activity and phosphatidylserine content by ceramic implant materials during endosteal bone healing," Calcif. Tissue (1992) 51:429–437). Hydroxyapatite implants behave like bone-bonding implants in that there is a stimulation of matrix vesicle enzymes, increased phosphatidylserine content and increased numbers of matrix vesicles (Schwartz, Z. et al., "Effects of hydroxyapatite implants on primary mineralization during rat fibial healing: biochemical and morphometric analysis," J. Biomed. Mater. Res. 27:1029–1038).

Biodegradable polymeric scaffold systems seeded with cells are useful for culture of specific types of cells in vitro. U.S. Pat. No. 4,963,489 to Naughton et al. issued Oct. 16, 1990 for "Three-Dimensional Cell and Tissue Culture System," incorporated herein by reference, discloses the use of a polymeric matrix for culture of cells such as skin, liver, pancreas, bone marrow, osteoblasts and chondrocytes, etc. in vitro. The seeded matrix may be transplanted in vivo.

Related U.S. Pat. No. 5,032,508 to Naughton et al. for "Three-Dimensional Cell and Tissue Culture System," also incorporated herein by reference, contains a similar disclosure. A further related U.S. Pat. No. 5,160,490 to Naughton et al. issued Nov. 3, 1992 for "Three-Dimensional Cell and Tissue Culture Apparatus," incorporated herein by reference, discloses that hip prostheses coated with three-dimensional cultures of cartilage may be implanted into patients. This patent also discloses that proteins can be "added to" the matrix or coated on.

SUMMARY OF THE INVENTION

This invention provides compositions and methods useful in wound healing. One such composition comprises matrix vesicles and/or matrix vesicle extract and Regulator of Enhancing Factor (REF). Another such composition also comprises latent growth factor in addition to the matrix vesicles and REF. A further composition comprises latent growth factor in combination with matrix vesicles and/or matrix vesicle extract. Further compositions of this invention comprise latent growth factors in combination with REF which are applied to a medium comprising matrix vesicles.

Matrix vesicles are membrane-bounded bodies secreted by cells involved in matrix formation, such as bone, cartilage and tendon cells. The matrix vesicles contain enzymes, hormones, and other factors which aid in matrix formation and which stimulate the cells in an autocrine manner. As secreted by the cells, they do not contain genetic material. Matrix vesicles may be isolated from a mammalian source, preferably from the patient (which may be a human or other mammal) to be treated with the matrix vesicles. A source of the same species, preferably a source known to be histo-compatible with the patient, may also be used. Procedures for isolating matrix vesicles are described herein. Matrix vesicles may also be synthesized as described herein. Matrix vesicle extract may be used in place of matrix vesicles and may be prepared from isolated matrix vesicles as described herein.

The compositions of this invention enhance wound healing when targeted to a wound site, preferably a cartilage or bone wound site. The compositions may be administered by means known to the art such as injection in a suitable pharmaceutical carrier, encapsulation in microspheres, e.g. for timed release, or incorporation into a biodegradable implant such as those described in U.S. patent application Ser. No. 08/123,812 filed Sep. 20, 1993, and corresponding PCT publication WO/9315694, published Aug. 19, 1993, and U.S. Pat. No. 08/196,970 filed Feb. 15, 1994, all of which are incorporated herein by reference. Preferably the compositions are incorporated into a timed release implant providing for release of the composition at the appropriate time during the wound healing. The implant may be a continuous release implant or may provide for release of the composition at specific times during wound healing for appropriate activation of the matrix. For example, Schmitz et al. (Acta Anatomica (1990) 138:185–192) have shown that critical size defects in the cranium of rats fail to heal. The failure of bone to form is evident 17 days post surgery, indicating that intervention must occur before this time. As known to the art, an initial burst of active growth factor is required for optimal healing in some instances. In other cases, continuous steady release is preferred. Implants of this invention incorporating latent growth factor may be designed to provide an initial burst of released latent growth factor or a continuous steady release of latent growth factor. Extraneous REF and matrix vesicles or extraneous matrix vesicle extract may be added to the wound site at the desired times, e.g. initially within 24 hours to provide an initial burst of active growth factor and/or when cell differentiation is desired, such as after about three days, and at about three-day intervals up to about 17 days.

The composition may also be used in vitro to stimulate growth and differentiation of cells, preferably osteoblasts or chondrocytes, in cell culture. It may also be incorporated onto scaffolding material for cell growth for later implantation into the host such as that described in U.S. Pat. Nos. 4,963,489, 5,032,508, and 5,160,490 to Naughton et al., also incorporated herein by reference.

REF is a substance which acts upon matrix vesicles to cause release of activating factors for growth factors, such as TGFβ activating factor. As discussed above, TGFβ is produced in latent form by many cell types and consists of a homodimer of 100 kD bound to an additional protein which may be a binding protein. TGFβ activating factor is a protease contained within matrix vesicles which releases the 100 kD active form of TGFβ.

As is known to the art, other growth factors are also produced in naturally latent form or may be synthesized in latent form. Such growth factors include insulin-like growth factors, fibroblast growth factors, bone morphogenetic proteins, and platelet-derived growth factors.

Matrix vesicles contain growth factor activating factors which, upon release from matrix vesicles stimulated with REF, activate such latent growth factors.

Some REFs are produced in vitro by the cells which produce matrix vesicles, and, as described in this invention, may also be added to a medium containing matrix vesicles either in vivo or in vitro to enhance release of factors which convert growth factors from latent to active form. As the matrix vesicles in their natural state contain no genetic machinery, the REFs act in a non-genomic manner, e.g., by altering membrane fluidity. Examples of REFs include vitamin D metabolites such as 1,25-dihydroxy-vitamin D (1,25-$(OH)_2D_3$). When 1,25-$(OH)_2D_3$ is used to stimulate activation of growth factor in vitro, it is preferably applied to cartilage cells in the growth zone stage of maturation or to differentiated osteoclasts.

When it is desired to stimulate activation of growth factor in resting zone stage cells, 24,25 dihydroxy-vitamin D (24,25-$(OH)_2D_3$) or active TGFβ may be used in combination with 1,25-$(OH)_2D_3$ to stimulate production of matrix vesicles. The 24,25-$(OH)_2D_3$ stimulates new matrix vesicle production by the cells through a genomic mechanism. When 24,25-$(OH)_2D_3$ is used directly on matrix vesicles, it may regulate the rate at which they are activated by inhibiting breakdown of the matrix vesicle membrane.

Steroid hormones are another class of REF, including estrogen, e.g. 17-beta-estradiol, testosterone, and dexamethasone. Thyroid hormone ($T_3$) is also considered to be a REF.

Prostaglandins and other lipophilic mediators of membrane action such as leukotrienes and platelet activating factor comprise a useful class of REFs.

The components of the compositions of this invention are present in pharmaceutically effective amounts, which means amounts effective to convert latent growth factor to active growth factor in measurable quantities, such that measurable effects on wound healing and tissue growth and/or differentiation occur. A pharmaceutically effective amount of REF is an amount sufficient to stimulate release by matrix vesicles of TGFβ activating factor in an amount sufficient to convert latent TGFβ to active TGFβ. Such amounts of REF may vary from minimal amounts necessary to produce a measurable amount of active TGFβ, assayed directly or by means of enhancement of wound healing, to a maximal amount equalling or exceeding the amount necessary to convert all latent TGFβ to active form.

In a preferred embodiment involving the use of 1,25-(OH)$_2$D$_3$, a $10^{-8}$ to $10^{-12}$M solution is used, preferably a $10^{-8}$ to $10^{-9}$M solution. Such a solution incubated with a suspension of matrix vesicles containing 1.6 mg protein per ml will activate a measurable amount of latent TGFβ, i.e. use of 8 µl of a $10^{-7}$M solution of 1,25-(OH)$_2$D$_3$ in 80 µl of the matrix vesicle suspension, resulting in a final concentration of $10^{-8}$M 1,25-(OH)$_2$D$_3$, will activate 0.6 ng/ml of latent TGFβ. When latent growth factors other than TGFβ are present, analogous molar ratios of matrix vesicles and REFs are used. Similarly analogous molar ratios of REFs other than 1,25-(OH)$_2$D$_3$ may be used. The REF may be injected locally into a healing wound, incorporated into an implant, or delivered by other means known to the art.

In healing bone and cartilage defects, matrix vesicles are present in a concentration of about 2–10 µg per µm$^2$ area of matrix. In a growing culture of bone or cartilage cells, matrix vesicles are naturally present at a concentration of about 5–50 µg matrix vesicle protein per 150 cm$^2$ of confluent monolayer cells. When REF is added to a healing wound or culture, it is preferably added in an amount sufficient to stimulate matrix vesicles present to release TGFβ activating factor, e.g., in an amount of about 100 pico M/cm$^3$.

When extraneous matrix vesicles are added to a defect in vivo or to a culture, they are added in amount which will produce measurable enhancement of wound healing or activation of latent TGFβ. A useful amount of matrix vesicles is between about 10 ng/cm$^3$ and about 2.0 mg/cm$^3$, preferably between about 1.8 mg/cm$^3$ and about 1.4 mg/cm$^3$ and more preferably between about 1.5 and about 1.7 mg/cm$^3$. Matrix vesicle extract may be used instead of or in addition to whole matrix vesicles. A useful amount of matrix vesicle extract is between about 200 µg protein/cm$^3$ and about 800 µg protein/cm$^3$, preferably between about 400 and about 600 and more preferably between about 450 and about 550.

REF may be added in addition to matrix vesicles, preferably at a ratio to the added matrix vesicles as set forth above, i.e. about 1:10 by volume of REF solution to matrix vesicle suspension, said REF solution having a concentration between about $10^{-8}$ and about $10^{-12}$M and said matrix vesicle suspension having about 1.6 mg protein/ml.

The inventors have discovered that resting zone chondrocytes are activated by the vitamin D metabolite 24,25-(OH)$_2$D$_3$. The methods of this invention include pretreatment of cultures and/or healing wounds to activate cell differentiation prior to treatment with 1,25-(OH)$_2$D$_3$ or other REFs and/or matrix vesicles or matrix vesicle extract. Preferably such pre-treatment occurs about 36 to 72 hours prior to treatment with 1,25-(OH)$_2$D$_3$ or other REFs. Preferably the pre-treatment includes serum such as fetal bovine serum (FBS).

Some agents inhibit matrix vesicles. For example, 24,25-(OH)$_2$D$_3$ inhibits some matrix vesicle enzymes which may be important for the release of growth factor activating factor.

This invention also provides matrix vesicles which have been treated so as to incorporate REF into their membranes. Preferably, such matrix vesicles are incubated with the desired REF, preferably 1,25-(OH)$_2$D$_3$, so that the REF is intercalated into the matrix vesicle membrane as described herein. The REF does not act immediately to break down the membrane, but rather the membrane breaks down over time to allow delivery of growth factor activating factors into the cellular matrix at a controlled rate. Varying the phospholipid composition of the matrix vesicles allows control of the release of the REF.

Latent growth factor capable of being converted to active form by matrix vesicle secretions containing growth factor activating factor may be added to a healing wound or culture. Wound healing and cell growth and/or differentiation are stimulated by activation of the latent growth factor by means of added REF and/or matrix vesicles, or matrix vesicle extract. The latent growth factor should be added in an amount sufficient to provide measurable enhancement of wound healing or culture growth and/or differentiation. Preferably, it is added in an amount between about 1 and about 2000 ng per cc of wound or culture volume, more preferably in an amount between about 10 and about 1000 ng and most preferably in an amount between about 50 and about 500 ng.

The administration of latent growth factors to healing wounds and to cell cultures for stimulation of cell growth and differentiation is especially useful when it is desired to control the timing of activation of the growth factor, for example so as to favor proliferation versus differentiation at appropriate times. By activating the growth factor responsible for regulating each event, cells can be modulated in a manner that is more physiological than present technology permits.

Matrix vesicles and/or REF may also be added in combination with the latent growth factor, in amounts as set forth above.

This invention also provides biodegradable polymeric implants or scaffolding materials (referred to generically herein as implant materials) comprising latent growth factors, REF, matrix vesicles or matrix vesicle extract in pharmaceutically effective amounts. Pharmaceutically effective amounts of latent growth factor are amounts sufficient to stimulate cell proliferation and/or differentiation upon activation during use. A preferred implant of this invention comprises between about 0.1 µg and about 2,500 µg latent growth factor per cc of polymeric material, or between about 10 pmoles and about 1000 pmoles REF per cc of polymeric material, or between about 10 ng and about 1000 ng of matrix vesicle protein per cc of polymeric material, or between about 5 ng and about 500 ng of matrix vesicle extract per cc of polymeric material. Any combination of latent growth factor, REF, matrix vesicles and matrix vesicle extract may be incorporated into such implant material, and the remaining components necessary for activation of latent growth factor may be added to the culture or wound site separately.

It is preferred that the polymeric implant material be designed for controlled release of the active components. Such polymeric implant materials are known to the art and are described hereinabove. In one embodiment, the polymeric implant is designed to continuously release active ingredients over its entire degradation period, as described in U.S. patent application Ser. No. 08/196,970 incorporated herein by reference.

The polymeric implant material may also comprise cells compatible with the host for which it is intended, for example as described in the above-referenced Naughton et al. patents.

This invention also provides a method for stimulating activation of a latent growth factor in a cellular matrix, which matrix comprises matrix vesicles, comprising contacting said matrix vesicles with a pharmaceutically effective amount of REF. If desired, additional latent growth factor may be added to the cellular matrix along with a sufficient amount of REF to activate it. Additional matrix vesicles or matrix vesicle extract may also be added.

This invention further provides a method of converting a growth factor or other cytokine from latent to active form comprising adding to a medium containing said growth factor in latent form matrix vesicles and/or matrix vesicle extract in an amount sufficient to activate said growth factor. REF may also be added to the medium along with matrix vesicles in an amount sufficient to convert said growth factor from latent to active form.

The method may be performed in vitro or in vivo. When the method is performed in vitro, it may be performed by adding matrix vesicles or matrix vesicle extract to a medium containing latent growth factor, or to a cell culture comprising latent growth factor. Cultures of cartilage, bone and tendon cells may be treated with the addition of matrix vesicles or matrix vesicle extract, as may defects in cartilage, bone and tendon tissue. When matrix vesicles are added to a medium containing latent growth factor which does not contain cells, it will be necessary to stimulate release of growth factor activating factor from the matrix vesicles by adding an effective amount of REF. When matrix vesicle extract is used, REF may not be required.

In methods involving activation of latent growth factor in cellular matrices in vivo or in vitro to which latent growth factor has been added, matrix vesicles may be provided by stimulating the cells with electricity, ultrasound or physical stress sufficient to increase production of matrix vesicles by the cells. REF in an amount sufficient to activate said latent growth factor may also be provided to the cellular matrices.

Healing of a wound, preferably a bone or cartilage defect, may be enhanced by a method of this invention comprising locally administering to said defect a composition comprising matrix vesicles or matrix vesicle extract in an amount sufficient to activate latent growth factor present in said defect. REF may also be added in an amount sufficient to stimulate said matrix vesicles to produce TGFβ activating factor. If desired, additional latent growth factor may also be added to the defect.

Healing of such wounds may also be enhanced by treating the defect with electrical energy in an amount sufficient to stimulate production of matrix vesicles or with ultrasound, physical stress or other means known to the art in an amount sufficient to stimulate production of matrix vesicles.

These healing methods may involve implanting into the wound or defect a biodegradable polymeric implant comprising an amount of latent growth factor sufficient to stimulate cell proliferation and/or differentiation upon activation during use.

BRIEF DESCRIPTION OF THE FIGURES

FIG. 1 is a diagram showing cellular production of matrix vesicles and factors regulating cells and matrix vesicles.

DETAILED DESCRIPTION OF THE PREFERRED EMBODIMENTS

Figure 2A:
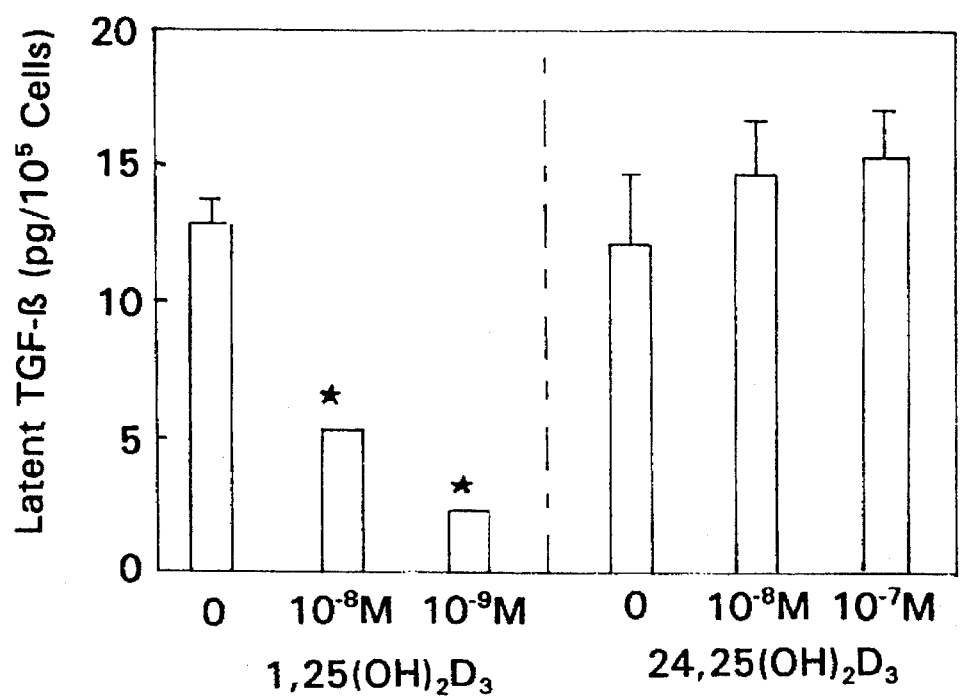
FIG. 2 shows the effect of $1,25-(OH)_2D_3$ on latent TGFβ production by growth zone chondrocytes. Treatment of growth zone chondrocytes with $1,25-(OH)_2D_3$ at $10^{-8}$ and $10^{-9}$M significantly inhibits the production of latent TGFβ by these cells. $24,25-(OH)_2D_3$ had no effect on latent TGFβ production. Panel a=pg latent TGFβ/$10^5$ cells from a single representative experiment; Panel b=treatment/control ratios derived from four additional experiments; *=treatment v. control or T/C v. 1, $P \leq 0.05$.

As shown in FIG. 1, a number of factors affect cellular production of matrix vesicles and REFs, and matrix vesicles themselves can be stimulated by REFs to release growth factor activating factors. New protein is synthesized within the cells, proteins are incorporated into the membranes and matrix vesicles are released.

Specifically, FIG. 1a depicts a cell 10, such as a cartilage, bone, or tendon cell, preferably a chondrocyte or osteoblast, containing a nucleus 12, rough endoplasmic reticulum 14, and golgi bodies 16.

The cell 10 may be stimulated by endogenous or added growth factors including TGFβ 18 which regulate the cell, REFs such as $1,25-(OH)_2D_3$, and $24,25-(OH)_2D_3$ and steroid hormones such as estrogen and testosterone. Electrical energy 22, ultrasound 24 or physical stress may be applied to cell 10 to stimulate production of matrix vesicles 28 and promote wound healing. Peptide hormones 26, endogenous or added, also regulate the cell 10.

The stimulated cell 10 produces matrix vesicles 28 and latent growth factor 30 as well as vitamin D metabolites 32 such as $1,25-(OH)_2D_3$ and $24,25-(OH)_2D_3$.

The vitamin D metabolites 32, specifically $1,25-(OH)_2D_3$, act on the matrix vesicle 28 shown enlarged in FIG. 1b surrounded by collagen 35 and proteoglycans 36. Other REFs 34 which may be produced by the cell or matrix vesicles or added to the system, and which can include added $1,25-(OH)_2D_3$, act on the matrix vesicle. The REFs 34 and vitamin D metabolites 32 produced by cell 10 act on matrix vesicle 28 to cause release of growth factor activating factors 42 (indicated by black arrow) to convert latent growth factors 30 to active growth factors 40.

This invention is based on the discovery that latent growth factor can be converted to active form by matrix vesicle extract or through the medium of matrix vesicles stimulated with REF.

These components can be added to healing wounds by direct injection or by means of implants or cell-seeded scaffolds cultured in vitro. This combination can also be used to stimulate cell growth and differentiation in cell cultures.

This discovery is specifically described in detail in the following examples using TGFβ as the growth factor, $1,25-(OH)_2D_3$ as the REF, and isolated matrix vesicles from chondrocyte cultures incubated with $1,25-(OH)_2D_3$.

As will be appreciated by those skilled in the art, substitutions of additional growth factors, REFs and matrix vesicle materials as described herein and as known to the art may be made as equivalents to the preferred embodiments described in detail herein.

The following examples provide detailed enablement for the compositions and methods of this invention.

EXAMPLES

Example 1

Activation of Latent TGFβ by 1,25-(OH)$_2$D$_3$

The aim of this study was to examine the production of TGFβ by vitamin D metabolites and TGFβ. The model has the advantage of allowing comparison of chondrocytes at two different stages of cell maturation. In addition, by using matrix vesicles isolated from these cultures, we can determine what role non-genomic regulation plays in TGFβ activation in the extracellular matrix. The results demonstrate that extracellular matrix vesicles derived from growth zone chondrocytes have the capacity to activate latent TGFβ; that production and activation of TGFβ by these chondrocytes is regulated by 1,25-(OH)$_2$D$_3$; and that the effect of 1,25-(OH)$_2$D$_3$ is cell maturation-dependent occurring through a non-genomic mechanism.

Dulbecco's modified Eagle's medium (DMEM), fetal bovine serum (FBS), antibiotics (penicillin, streptomycin, fungizone), trypsin, and other tissue culture reagents were from GIBCO Laboratories (Grand Island, N.Y.). Collagenase (Type II) was purchased from Worthington (Freehold, N.J.). 24R,25-(OH)$_2$D$_3$ and 1α,25-(OH)$_2$D$_3$ were kind gifts of Dr. Milan Uskokovic (Hoffman LaRoche, Nutley, N.J.). Recombinant simian latent TGFβ$_1$ and TGFβ$_2$ were prepared as described below. Recombinant human TGFβ$_1$ and specific antibodies to TGFβ or TGFβ$_2$ were purchased from R & D Systems (Minneapolis, Minn.). Spin-X filters were purchased from Costar (Cambridge, Mass.); reagents for Northern analysis, including Nitroplus 2000 filters, were purchased from Micron Separation, Inc. (Westborough, Mass.); guanidine thiocyanate was purchased from Fluka, Inc. (Ronkonkoma, N.Y.). The human TGFβ$_1$ cDNA (1.1 kb) used to prepare radioactive probes was a gift from Genentech, Inc. The glyceraldehyde-3-phosphate dehydrogenase (GAPDH) cDNA probe was isolated from a pHcGAP clone obtained from the American Type Culture Collection (Bethesda, Md.).

The culture system used in this study has been described in detail previously (Boyan, B. D., et al. (1988) Bone 9:185–194). Briefly, rib cages were removed from 125 g Sprague-Dawley rats by sharp dissection and placed in DMEM until microdissection could be performed. The resting zone and adjacent growth zone cartilage were separated, and care was taken to dissect out intervening tissue so that cross contamination of cell zones would be decreased. Perichondrium and calcified cartilage were discarded to limit contamination by fibroblasts, osteoblasts, and osteoclasts.

When the dissection was complete, cartilage from each zone was sliced, placed in DMEM containing 10% FBS and incubated overnight in a 5% CO$_2$ atmosphere at 37° C. The DMEM was then replaced by two 20-minute washes of Hank's balanced salt solution (HBSS), followed by sequential incubations in 1% trypsin for one hour and 0.02% collagenase for three hours. After enzymatic digestion of the extracellular matrix was complete, cells were separated from tissue debris by filtration through 40-mesh nylon and collected from the filtrate by centrifugation at 500× g for ten minutes, resuspended in DMEM, counted and plated at an initial density of 10,000 cells/cm$^2$ for resting zone cells or 25,000 cells/cm$^2$ for growth zone cells.

Cells were incubated in DMEM containing 10% FBS, 1% penicillin-streptomycin-fungizone, and 50 μg/ml vitamin C in an atmosphere of 5% CO$_2$ at 37° C. and 100% humidity for 24 hours. The culture medium was replaced at that time and then at 72-hour intervals until the cells reached confluence. At confluence, cells were subcultured to T75 flasks at the same plating densities as before and allowed to return to confluence. Cells were only subcultured a maximum of three times to ensure retention of phenotype. Fourth passage cells were used for all experiments. Previous studies have shown that these cells retain their chondrocytic phenotype and differential responsiveness to 1,25-(OH)$_2$D$_3$ and 24,25-(OH)$_2$D$_3$.

Vitamin D metabolite stock solutions were prepared by using ethanol as the solvent. Before addition to the cultures, each hormone stock solution was diluted at least 1:5000 (v/v) to minimize any toxic effects of ethanol. For the experiments, final concentrations were $10^{-8}$M or $10^{-9}$M 1,25-(OH)$_2$D$_3$ or $10^{-7}$M or $10^{-8}$M 24,25-(OH)$_2$D$_3$. Each experiment included control cultures that contained ethanol at the highest concentration used in the vitamin D metabolite-treated groups.

Fourth passage cells were cultured in 24-well culture dishes as described above. At confluence, the medium was replaced with DMEM containing 10% FBS, antibiotics, ascorbic acid, and appropriate concentrations of vitamin D metabolites. Medium was also added to 24-well plates without cells to measure the amount of active and latent TGFβ derived from 10% FBS. At harvest, media were analyzed for their content of both active and latent TGFβ. The cell layers were trypsinized (1% trypsin), the cells counted, and the amount of TGFβ per ml or $10^5$ cells calculated.

TGFβ activity was assayed by stimulation of alkaline phosphatase specific activity in cultures of ROS 17/2.8 cells. This microassay was performed as described previously (Schwartz, Z., et al., Endocrinology (1993) 132:1544–1552; Bonewald, L. F., et al., Mol. Endocrinol. (1991) 5:741–751; Oreffo, R.O.C., et al., Biochem. Biophys. Res. Comm. (1989) 153:817–823). The CCL64 mink lung epithelial cell assay was also performed as described by Danielpour et al. (Danielpour, D. et al., J. Cell. Physiol. (1989) 138:79–86) and is based on the ability of TGFβ to inhibit [$^3$H]-thymidine incorporation by these cells. A TGFβ standard curve (0.02 to 5 ng/ml) was performed in each assay. Specificity for TGFβ1 or TGFβ2 was confirmed by neutralization of activity with specific antibodies to TGFβ1 or TGFβ2.

To determine the amount of latent TGFβ, conditioned media were acid-activated by addition of 4 μl 4N HCl to 100 μl of the medium and incubation for 15–20 minutes at 20° C. The reaction was then neutralized by addition of 4 μl 4N NaOH, aseptically filtered using Spin-X filters, and TGFβ activity in the filtrate measured as described above. The amount of latent TGFβ was determined by subtracting the amount of activity in the pre-acidified samples from the total activity following acid activation.

Total cellular RNA was isolated from fourth passage, confluent cultures of growth zone and resting zone chondrocytes by lysing cells in guanidinium thiocyanate, followed by phenol:chloroform extraction (Chomczynski, P. and Sacchi, N., Anal. Biochem. (1987) 162:156–159). Poly (A$^+$) RNA was obtained by fractionating total RNA using oligo(dT) cellulose chromatography. Northern blot analysis was performed as described by Fourney et al. (Fourney, R. M. et al., Bethesda Res. Lab, Inc. Focus (1988) 10:5–7), with a modified procedure for formaldehyde agarose gel electrophoretic separation of RNA (Lehrach, H. et al., Biochemistry (1977) 16:4743–4751; Davies, L. G. et al., in: *Basic Methods in Molecular Biology*, Elsevier, New York, N.Y. (1977) 143–149). Preparations of RNA loaded onto 1% agarose gels were electrophoresed at 4 volts/cm gel length for six hours and transferred to Nitroplus 2000 filters in 10× SSC at room temperature. The filter was baked at 80° C. under vacuum and prehybridized in 50% formamide, 5× SSPE, 5× Denhardt's buffer, and 250 µg/ml denatured *E. coli* DNA at 37° C. for three to five hours. The filter was then hybridized at 37° C. overnight in the same solution containing 10% dextran sulfate and $^{32}$P-labeled probe. The cDNA probes were labeled with $^{32}$P as described by Feinberg and Vogelstein (Feinberg, A. P. and Vogelstein, B. Anal. Biochem. (1983) 132:6–13). After hybridization, filters were washed and autoradiographed (Fourney, R. M. et al., Bethesda Res. Lab, Inc. Focus (1988) 10:5–7). The RNA blots were analyzed by a Beta Scope 603 Blot Analyzer (Betagen, Waltham, Mass.). Relative intensities of the hybridization signals were calculated with the aid of a GS 370 program (Hoefer Scientific Instruments, San Francisco, Calif.). The relative amount of mRNA loaded in each lane of the agarose gel was determined by the amount of GADPH mRNA detected in each lane. Filters were stripped in 50% formamide containing 10 mM Tris, 1 mM ethylenediamine tetraacetic acid (EDTA), and 0.1% sodium dodecyl sulfate (SDS) at pH 7.5 for two to four hours at 65° C. before hybridization with a second probe.

Matrix vesicles were prepared from chondrocyte cultures as described previously (Boyan, B. D., et al., Bone (1988) 9:185–194). At harvest, the conditioned media were decanted, and the cells were released by trypsinization (1% in HBSS). The reaction was stopped with DMEM containing 10% FBS, and the cells were collected by centrifugation at 500× g for 10 minutes, resuspended in saline, washed twice, and counted. The supernatant from the trypsin digest was centrifuged for 20 minutes at 13,000× g to pellet a mitochondria/membrane fraction, and the resulting supernatant was centrifuged for one hour at 100,000× g to pellet matrix vesicles. Matrix vesicles were resuspended in 1 ml 0.9% NaCl. Detergents such as Triton X-100 were not used to solubilize the membranes, since they inhibit phospholipase $A_2$, an enzyme which is sensitive to vitamin D metabolites. All samples used in subsequent assays represent the combination of three cultures (i.e., three T75 flasks). The protein content of each fraction was determined (Lowry, O. H. et al., J. Biol. Chem. (1951) 193:265–275).

Alkaline phosphatase [orthophosphoric monoester phosphohydrolase alkaline (EC 3.1.3.1)] was measured as a function of the release of para-nitrophenol from para-nitrophenylphosphate at pH 10.2 (Bretaudiere, J. P. and Spillman, T., In: *Methods of Enzymatic Analysis*, Bergmeyer, H. U. (ed.), Verlag Chemica, Weinheim, Germany (1984) Vol. 4, 75–93). These techniques resulted in matrix vesicle preparations that were enriched in alkaline phosphatase-specific activity that was two to ten times greater than that of the plasma membrane. Previous studies have shown that there is a differential distribution of other plasma membrane marker enzymes in matrix vesicles and that contamination of other organelles in either membrane preparation is minimal.

Preparation of Recombinant Latent TGFβ. The source of latent TGFβ for these experiments was $NH_4SO_4$ precipitated protein derived from Chinese Hamster ovary (CHO) cells transfected with the gene coding for either simian TGFβ1 (Gentry, L. E. et al., Mol. Cell. Biol. (1987) 7:3418–3427) or TGFβ2 (Madisen, L. et al., Growth Factors (1990) 3:129–138). The recombinant TGFβ1 preparation was >90% latent and contained approximately 60–100 ng/ml of latent TGFβ. The recombinant TGFβ2 preparation was also >90% latent and contained approximately 150–200 ng/ml of latent TGFβ.

Activation of Latent TGFβ by Chondrocytes. These experiments were performed as described by Oreffo et al. (Oreffo, R.O.C., et al., Biochem. Biophys. Res. Comm. (1989) 153:817–823) except that chondrocytes were incubated with recombinant simian latent TGFβ-instead of latent TGFβ purified from bone. Resting zone and growth zone chondrocytes were cultured to confluence, the media removed, and DMEM containing 1% FBS, ascorbic acid, antibiotics, and recombinant latent TGFβ1 (0.6 ng/ml)±1, 25-$(OH)_2D_3$ ($10^{-7}$M) or 24,25-$(OH)_2D_3$ ($10^{-6}$M) was added. Cultures were incubated for 24 hours at 37° C. in an atmosphere of 5% $CO_2$. Antibody specific for TGFβ1 was used to prove specificity. The conditioned media were then tested for their content of active and latent TGFβ in the ROS 17/2.8 alkaline phosphatase microassay.

Activation of Latent TGFβ by Isolated Matrix Vesicles. Matrix vesicles were diluted to 1.6 mg protein/ml in PBS. All incubations were performed in 96-well microtiter plates in a total volume of 200 µl. First, 80 µl of the matrix vesicle suspension were added, followed by 8 µl of either $10^{-7}$M 1,25-$(OH)_2D_3$ or $10^{-6}$M 24,25-$(OH)_2D_3$ in DMEM containing 2% FBS, resulting in a $10^{-8}$M or $10^{-7}$M concentration, respectively. The plate was incubated for three hours at room temperature. After the matrix vesicles had been pre-incubated with vitamin D, recombinant simian latent TGFβ1 or TGFβ2 was added and the incubation continued for an additional 24 hours at room temperature. TGFβ activity was then measured using the ROS 17/2.8 microassay. To ensure that changes in alkaline phosphatase specific activity were entirely due to active TGFβ, pan-neutralizing antibody for all TGFβ isoforms was added at 40 µg/ml (sufficient to block 2 ng/ml TGFβ) and incubated for 30 minutes before addition of the samples to the ROS 17/2.8 cells.

The data are from representative experiments and are expressed as mean ± standard error of the mean. For any particular experiment, each data point represents six individual cultures. For studies using matrix vesicles (n=3), each "n" represents the matrix vesicles isolated from two to three T-75 flasks. Data were analyzed by analysis of variance with statistical significance between treatment and control being assessed by Bonferroni's modification of the t-test. To verify the consistency of the observations, experiments were repeated two or more times. Treatment/control ratios were derived from five or more independent experiments and were compared using the Wilcoxon2.

Virtually all TGFβ present in the conditioned media produced by either growth zone or resting zone chondrocytes was in latent form. In the present study, growth zone chondrocytes produced 12.90±0.7 ng latent TGFβ/ml or 8.2±1.7 pg/$10^5$ cells. In contrast, resting zone chondrocytes produced 9.7±0.6 ng latent TGFβ/ml or 4.8±0.5 pg/$10^5$ cells. Attempts to measure active TGFβ (i.e., activity prior to acidification of the conditioned medium) in these cultures were unsuccessful, even though the assay could detect active TGFβ at concentrations of 0.1 ng/ml or more.

Anti-TGFβ1 antibody inhibited the majority of the TGFβ activity in DMEM+10% FBS, as well as conditioned media, indicating that TGFβ1 was the predominant isoform produced by the chondrocytes. Anti-TGFβ2 antibody inhibited approximately 25% of the activity present in growth zone chondrocyte conditioned media, indicating that these cells also produced the TGFβ2 isoform. In contrast, resting zone chondrocytes only produced TGFβ1.

The production of latent TGFβ by growth zone or resting zone chondrocytes was unaffected by addition of rhTGFβ1 to the culture medium. Pan-neutralizing anti-TGFβ antibody blocked the activity of acid-activated culture media. In addition, no active TGFβ was detected when exogenous active TGFβ was added to the cells for 24 hours, growth factor-containing medium removed, and the conditioned media examined 24 or 48 hours later. Similarly, TGFβ1 mRNA levels were unaffected by addition of rhTGFβ1 to cultures of either cell type.

Figure 2B:
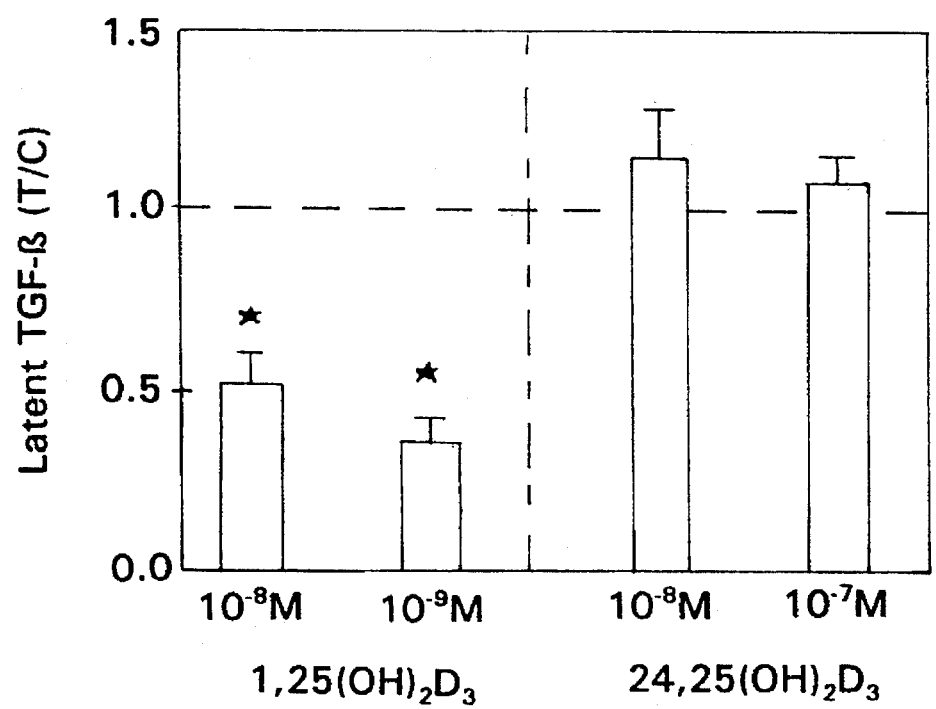

Treatment of growth zone chondrocytes for 24 hours with 1,25-$(OH)_2D_3$ significantly reduced the amount of latent TGFβ found in the conditioned media in a dose-dependent manner. This was true whether pre-confluent or confluent cultures were used. However, the effect of serum concentration in the medium was dependent on the confluency of the cells. 24,25-$(OH)_2D_3$ had no effect on the production of latent TGFβ by these cells (FIG. 2). Resting zone chondrocytes behaved in a similar manner, but to a lesser degree. As before, no active TGFβ could be detected in these cultures. 1,25-$(OH)_2D_3$ did not alter the level of mRNA for TGFβ1 in chondrocytes, as determined by Northern analysis using total RNA.

When exogenous latent TGFβ2 or TGFβ1 was added to either resting zone or growth zone chondrocyte cultures in the presence of 1,25-$(OH)_2D_3$ or 24,25-$(OH)_2D_3$, no active TGFβ was detected in the conditioned media. This indicates that no cellular activation of latent TGFβ occurred with 1,25-$(OH)_2D_3$ or 24,25-$(OH)_2D_3$ treatment.

Figure 3:
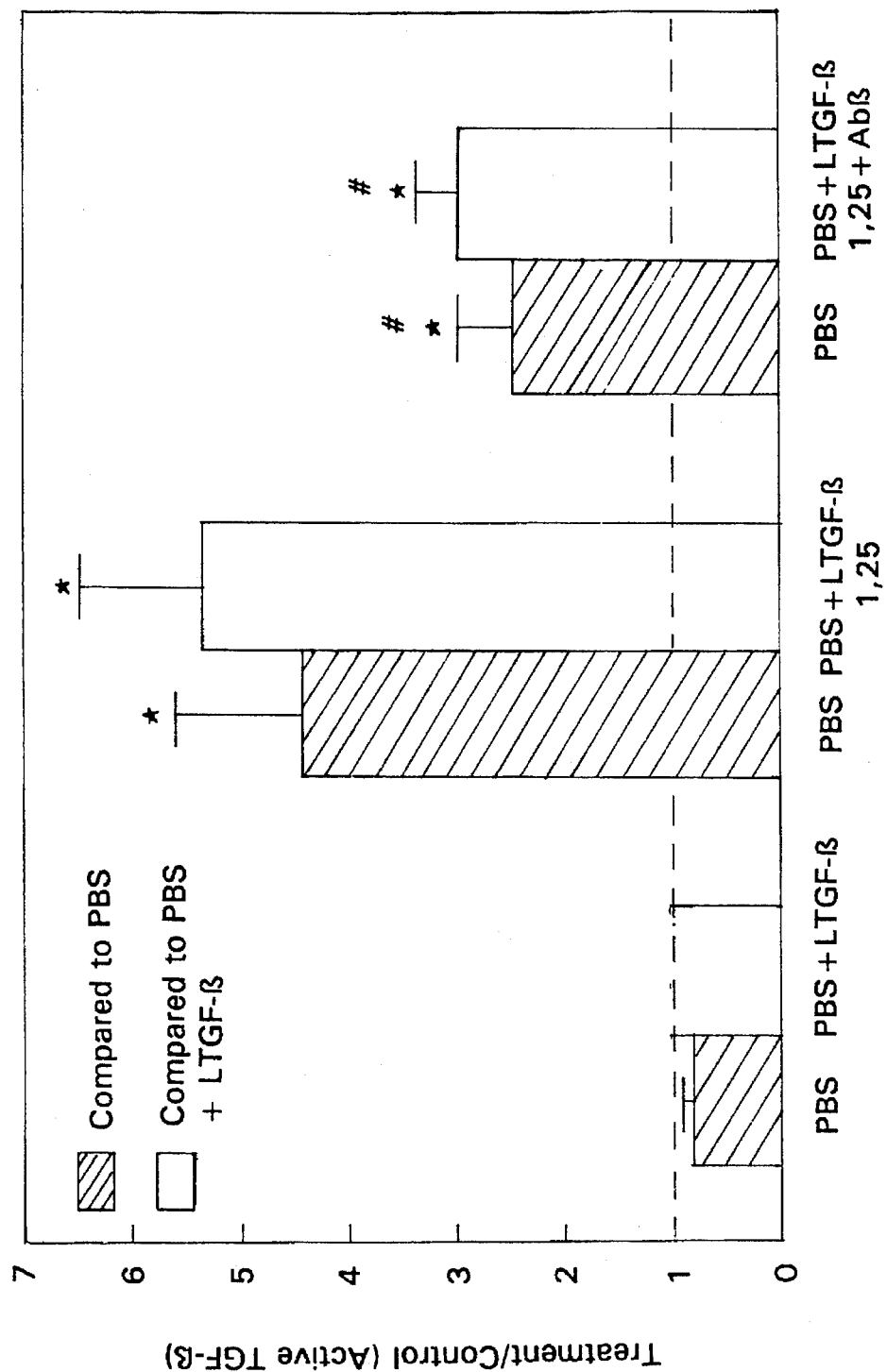
FIG. 3 shows treatment/control ratios for study showing activation of latent TGFβ by $1,25-(OH)_2D_3$-treated growth zone chondrocyte-derived matrix vesicles. Data from six experiments were combined and expressed as treatment/control ratios. No active TGFβ was detected in matrix vesicles or in matrix vesicles incubated with latent TGFβ. Recombinant latent TGFβ was activated by $1,25-(OH)_2D_3$-pretreated growth zone matrix vesicles; this was significantly inhibited by pan-neutralizing antibody (Abβ). *=significantly different from PBS+LTGFβ, p<0.05; #=significantly different from PBS+LTGFβ+1.25, p<0.05. LTGFβ=recombinant latent TGFβ; 1,25=$1,25-(OH)_2D_3$; Abβ=pan neutralizing antibody for TGFβ.

When matrix vesicles were isolated from cultures of growth zone or resting zone chondrocytes and assayed for their content of active TGFβ, no activity was found. Further, when exogenous latent TGFβ1 or TGFβ2 was added to these membrane fractions, no activation of latent growth factor occurred. Pretreatment of isolated matrix vesicles with 1,25-$(OH)_2D_3$ or 24,25-$(OH)_2D_3$, followed by incubation with latent TGFβ1, resulted in a detectable increase in active TGFβ in all samples; however, highly significant increases (4.4-fold) were only seen in matrix vesicles isolated from growth zone chondrocytes. The 1,25-$(OH)_2D_3$-dependent increase in active TGFβ was inhibited greater than 50% by pan-neutralizing TGFβ antibody. Depending on the experiment, matrix vesicles isolated from growth zone chondrocyte cultures activated 25–70% of the total latent TGFβ. Although total activation varied among experiments, a significant increase was always found after treatment with 1,25-$(OH)_2D_3$. Treatment/control ratios derived from five experiments showed a five-fold increase in TGFβ activation over control levels (FIG. 3). Activation of latent TGFβ2 was also regulated by 1,25-$(OH)_2D_3$ in a manner comparable to that seen for latent TGFβ1.

This study emphasizes the complex interactions that can occur between vitamin D metabolites and TGFβ. Costochondral chondrocytes, like epiphyseal chondrocytes, secrete primarily latent TGFβ of the β1 isoform. Unlike many other cell types, however, exogenously added TGFβ had no effect on TGFβ1 mRNA levels or on release of latent TGFβ into the conditioned media. 1,25-$(OH)_2D_3$ reduced the amount of latent TGFβ produced by chondrocytes, whereas, 24,25-$(OH)_2D_3$ had no effect. Furthermore, 1,25-$(OH)_2D_3$ had a direct effect on isolated matrix vesicles, inducing them to activate latent TGFβ.

Both TGFβ and vitamin D alone have significant effects on expression of the chondrocyte or osteoblast phenotype, but in conjunction, the effects can be dramatic. TGFβ and vitamin D have been shown to synergize with respect to alkaline phosphatase induction in bone cell lines, primary human bone cells, and rat resting zone chondrocytes. TGFβ may act as a "coupling" factor in bone remodeling, and vitamin D has been shown to be essential for proper endochondral ossification. The present data suggest that vitamin D can stimulate activation of latent TGFβ, thereby increasing the chance that both factors will be present simultaneously.

Both TGFβ and vitamin D regulate chondrocyte differentiation. Exogenous TGFβ stimulates DNA synthesis and matrix formation in chick growth plate chondrocytes. In rat growth plate chondrocytes, rhTGFβ1 regulates alkaline phosphatase, phospholipase $A_2$, and protein kinase C activities, as well as vitamin D metabolite production. Cellular response to TGFβ depends on the state of endochondral maturation, with resting zone cells exhibiting a differential response compared to that observed in growth zone cell cultures. Similarly, vitamin D metabolites also regulate the expression of alkaline phosphatase, phospholipase $A_2$, and protein kinase C in chondrocytes in a cell maturation-specific manner. These studies demonstrated that production of 1,25-$(OH)_2D_3$ and 24,25-$(OH)_2D_3$ is sensitive to TGFβ, and the actions of TGFβ and the vitamin D metabolites are interdependent. The present study demonstrates that latent TGFβ production and activation are sensitive to 1,25-$(OH)_2D_3$ and suggests a potential feedback mechanism.

Regulation of TGFβ production and activation in cartilage has not been previously described. In many cell types, synthesis of TGFβ is sensitive to exogenous TGFβ, suggesting an autocrine loop. Unlike these cell types, however, the costochondral chondrocytes do not appear to respond to exogenous TGFβ1 by increasing their levels of TGFβ1 mRNA or of either latent or active TGFβ in their conditioned media. This reproducibly occurs under the culture conditions used in this study. Using comparable culture conditions, the effect of TGFβ on chondrocyte alkaline phosphatase is ten times greater than that seen in osteoblast cell lines.

The failure of exogenous TGFβ to autoregulate TGFβ production by the chondrocytes may be an adaptive result of the high levels of this growth factor stored in cartilage. Although exogenous TGFβ may not have an autocrine effect on the production of latent TGFβ and its release into the culture media, it is likely in cartilage that such an autocrine loop is maintained by growth factor stored in the matrix in latent form and activated locally. The results of this study support this hypothesis.

We have previously shown that exogenous TGFβ1 regulates production of vitamin D metabolites by chondrocytes in a cell maturation-specific and time-dependent manner. The present study demonstrated an effect of 1,25-$(OH)_2D_3$ on TGFβ, resulting in a marked decrease in the amount of latent factor in the media. The effects of vitamin D were both metabolite-specific and cell maturation-dependent. There was a 1,25-$(OH)_2D_3$-dependent decrease in latent TGFβ in both chondrocyte populations, although the effect was greater in growth zone cell cultures. The role of 1,25-$(OH)_2D_3$ in this process appears to be specific, since 24,25-$(OH)_2D_3$ did not elicit a comparable response. The preincubation period was long enough for the chondrocytes to convert 24,25-$(OH)_2D_3$ to 24,25-$(OH)_2D_3$ (Schwartz, Z., et al., Endocrinology (1992) 130:2495–2504), further supporting the specificity of the 1,25-$(OH)_2D_3$ effect.

The data support the activation of existing latent TGFβ1 and TGFβ2 by matrix vesicles via direct interaction of 1,25-$(OH)_2D_3$ with the organelle. Active metalloproteinases present in matrix vesicles may be prime candidates for accomplishing this process. In growth plate, the immunohistochemical distribution of TGFβ1 coincides with the localization of matrix vesicles in the territorial matrix of the cells, providing support for potential activation of latent TGFβ in the matrix by matrix vesicle proteases.

The results of this study are consistent with the hypothesis that 1,25-$(OH)_2D_3$, secreted by the chondrocyte, regulates matrix vesicle via direct, nongenomic mechanisms. Matrix vesicle membrane fluidity and enzyme activity can be directly and specifically regulated by 1,25-$(OH)_2D_3$ in the absence of the cell and its molecular and protein synthetic machinery. In the present study, direct incubation of isolated matrix vesicles with 1,25-$(OH)_2D_3$ resulted in activation of latent TGFβ1, as well as latent TGFβ2. Matrix vesicles produced by osteoblast-like cells also contain matrix processing enzymes which indicates that a similar mechanism of TGFβ activation plays a role in bone, as well as cartilage.

In summary, these studies show that TGFβ and vitamin D metabolites have complex and interactive roles in chondrogenesis. The effects of these factors vary, depending on the stage of differentiation of the chondrocyte. TGFβ is produced in a latent form by these cells. Whereas autocrine effects have been observed with respect to chondrocyte phenotype expression, none were observed in the present study with respect to TGFβ messenger RNA levels or protein production in active or latent forms. In contrast, 1,25-$(OH)_2D_3$ reduces the level of latent TGFβ produced by these cells by an unknown mechanism, as messenger RNA was not affected, and activation of the latent form did not appear to be occurring, at least with respect to the conditioned media. Matrix vesicles are excellent targets for the nongenomic effects of vitamin D, as these are located in the matrix at a distance from the cell and adjacent to the mineralization front. In vitro, matrix vesicles are inert with respect to activation of latent TGFβ unless exposed to 1,25-$(OH)_2D_3$, which triggers the activation process.

Example b 2

Effects of 1,25-$(OH)_2D_3$ in calcium ion flux and Protein Kinase C activity

It is well accepted that 1,25-$(OH)_2D_3$ alters Ca ion flux in osteoblasts. However, little is known concerning the role of this vitamin D metabolite in chondrocytes, particularly with respect to its nongenomic action. Even less information is available concerning the effects of 24,25-$(OH)_2D_3$. To examine this, we characterized the uptake and release of $^{45}Ca$ by resting zone and growth zone chondrocytes in the presence of 1,25-$(OH)_2D_3$ and 24,25-$(OH)_2D_3$. At 1 minute, 24,25-$(OH)_2D_3$ inhibited $^{45}Ca$ efflux from resting zone cells and 1,25-$(OH)_2D_3$ stimulated $^{45}Ca$ efflux from growth zone cells.

Changes in arachidonic acid metabolism and Ca ion flux suggested that membrane signal transduction pathways might also be affected by vitamin D. To determine if this was the case, we assayed cultures for protein kinase C activity in the presence of inhibitors of gene transcription and translation. The results of the studies demonstrate that 1,25-(OH)$_2D_3$ stimulated protein kinase C activity in growth zone chondrocytes but had no effect on resting zone cells. In contrast, 24,25-$(OH)_2D_3$ stimulated enzyme activity in resting zone cells but had no effect on growth zone cells. Moreover, the time course of response was different. Stimulation was more rapid in the growth zone cells (9 to 90 minutes), but the effect of 24,25-$(OH)_2D_3$ on the resting zone cells was delayed but sustained over a longer time (90 to 360 minutes). The inhibitor studies demonstrated clearly that the 1,25-$(OH)_2D_3$-dependent effect was non-genomic, requiring no new gene transcription or translation, whereas both processes were required for the 24,25-$(OH)_2D_3$-dependent effect.

These studies showed that at the cellular level, the action of 24,25-$(OH)_2D_3$ involved genomic mechanism while the action of 1,25-$(OH)_2D_3$, at least at short time periods, did not. There remained the question of whether this enzyme activity was also found in matrix vesicles and, if so, if it could be regulated directly by the hormones. Our results show that protein kinase C-ζ is preferentially localized in matrix vesicles produced by both cell types. Anti PKCα antibody inhibits PKC activity in plasma membranes and anti PKC ζ antibody inhibits PKC activity in matrix vesicles. Both metabolites regulate matrix vesicle PKC ζ in a nongenomic manner. When matrix vesicles from growth zone cell cultures are incubated directly with 1,25-$(OH)_2D_3$ enzyme activity is inhibited. Similarly, when matrix vesicles isolated from resting zone cell cultures are incubated with 24,25-$(OH)_2D_3$ PKC ζ activity is decreased.

Both 1,25-$(OH)_2D_3$ and 24,25-$(OH)_2D_3$ can exert their effects on chondrocytes by nongenomic mechanisms. The actions include changes in membrane fluidity, phospholipid metabolism, Ca ion flux, and protein kinase C activity. Matrix vesicles are regulated independently of the cell. While their composition may be under genomic control, it is likely that once in the extracellular matrix they are regulated by direct action of vitamin D metabolites secreted by the chondrocyte.

Example 3

Activation of resting zone chondrocytes by 24,25-$(OH)_2D_3$.

Studies suggest that 24,25-$(OH)_2D_3$ has an important role in the early stages of chondrocyte differentiation, whereas 1,25-$(OH)_2D_3$ has an important role in the later stages of chondrocyte differentiation. Based on previous in vivo and in vitro observations, a hypothesis can be made that 24,25-$(OH)_2D_3$ induces resting zone chondrocytes to progress down the endochondral pathway and acquire a growth zone-like phenotype.

To test this hypothesis, we assessed whether resting zone cells acquired responsiveness to 1,25-$(OH)_2D_3$ following exposure to 24,25-$(OH)_2D_3$. The ability of 24,25-$(OH)_2D_3$-stimulated resting zone chondrocytes to respond to 1,25-$(OH)_2D_3$ was compared to that of authentic growth zone chondrocytes with respect to DNA synthesis, alkaline phosphatase activity, RNA synthesis, collagen and noncollagen protein synthesis, and proteoglycan production. To assess whether cells already in the endochondral lineage (i.e., from the resting zone to calcified cartilage) differ from hyaline chondrocytes in their response to 24,25-$(OH)_2D_3$, we also examined cells from the xiphoid process.

Fourth passage resting zone or xiphoid chondrocytes were grown to confluence. At confluence, the media were replaced with media containing $10^{-7}M$ 24,25-$(OH)_2D_3$ or vehicle alone for 24, 36, 48, 72 or 120 hours. For those cells pretreated for 120 hours, fresh media containing the appropriate concentration of 24,25-$(OH)_2D_3$ was added at 72 hours. At the end of the pretreatment period, the media were replaced again with medium containing 1,25-$(OH)_2D_3$ at a concentration of $10^{-10}$ to $10^{-8}M$ or vehicle alone and grown for an additional 24 hours. At that time, the cells were harvested and assayed as described below. To determine if the effect of pretreatment with 24,25-$(OH)_2D_3$ was metabolite-specific and not due to a general steroid hormone effect, resting zone cells were pretreated with $10^{-8}M$ 1,25-$(OH)_2D_3$ for 24, 36, 48, 72, or 120 hours, followed by treatment with $10^{-10}$ to $10^{-8}$M 1,25-(OH)$_2$D$_3$ and then assayed for alkaline phosphatase specific activity.

DNA synthesis by nonquiescent resting zone cells was estimated by measuring [$^3$H]-thymidine incorporation into trichloroacetic acid (TCA) insoluble precipitates (Langston, G. G. et al., "Effect of 1,25-(OH)$_2$D$_3$ and 24,25-(OH)$_2$D$_3$ on calcium influxes in costochondral chondrocyte cultures", Calcif. Tissue Int. (1990) 47:230–236). Chondrocytes were grown to confluence in 6 mm diameter microwells and [$^3$H]-thymidine (50 μl) added two hours prior to harvest so that the final concentration in the medium was 2 μCi/ml. At harvest, the cell layers were washed twice with cold phosphate-buffered saline, twice with 5% TCA, and then treated with saturated TCA for 30 minutes. TCA-precipitable material was dissolved in 0.2 ml 1% sodium dodecyl sulfate (SDS), and the radioactivity measured by scintillation spectroscopy.

Resting zone and xiphoid cells were cultured in 24-well culture dishes (Corning, N.Y.). At harvest, the media were decanted and the cell layers washed twice with phosphate-buffered saline (PBS) before removal with a cell scraper. Enzyme assays were performed using lysates of the cell layers (Schwartz, Z. et al., "Localization of Vitamin D$_3$ responsive alkaline phosphatase in cultured chondrocytes," J. Biol. Chem (1988) 263:6023–6026; Hale, L. V. et al., "Effect of vitamin D metabolites on the expression of alkaline phosphatase activity by epiphyseal hypertrophic chondrocytes in primary cell culture", J. Bone Min. Res. (1986) 1:489–495). After centrifugation, the cell layer pellet was washed two times with PBS and resuspended by vortexing in 500 μl deionized water containing 25 μl of 1% Triton X-100. Alkaline phosphatase [orthophosphoric monoester phospho-hydrolase alkaline (EC 3.1.3.1)] specific activity was measured as a function of para-nitrophenol release from para-nitrophenylphosphate at pH 10.2, as previously described (Bretaudier, J. P. and Spillman, T., "Alkaline phosphatases", In: Bergmeyer HU (ed) Methods Enzymatic Anal. Verlag Chemie, Weinheim (1984) 4:75–81).

RNA synthesis was estimated by measuring [$^3$H]-uridine incorporation into TCA-insoluble cell precipitates. Resting zone cells were grown to confluence in 6 mm diameter microwells and [$^3$H]-uridine (50 μl) added two hours before harvest so that the final concentration in the medium was 14 μCi/ml. From this point, the protocol described above for quantitating [$^3$H]-thymidine incorporation was followed exactly.

Incorporation of labeled proline into collagenase-digestible protein (CDP) and collagenase-nondigestible protein (NCP) was used to estimate matrix protein synthesis by resting zone cells (Raisz, L. G. et al., "Comparison of the effects of a potent synthetic analog of bovine parathyroid hormone with native bPTH-(1–84) and synthetic bPTH-(1–34) on bon resorption and collagen synthesis," Calcif. Tissue Int. (1979) 29:215–218). Percent collagen synthesis was calculated after multiplying the labeled proline in NCP by 5.4 to correct for its relative abundance in collagen (Beresford, J. N. et al., "1,25-Dihydroxyvitamin D$_3$ and human bone-derived cells in vitro: Effects on alkaline phosphatase, type I collagen and proliferation", Endocrinology (1986) 119:1776–1785).

Twenty-four hours before harvesting, 5 μCi of L-[G$^3$H]-proline (New England Nuclear, Boston, Mass.) in 1.0 ml medium was added. At harvest, the media were decanted and the cell layer collected in two 0.2 ml portions of 0.2N NaOH. Proteins present in the cell layer were first precipitated with 0.1 ml 100% TCA containing 10% tannic acid. The resultant precipitate was washed three times with 10% TCA-1% tannic acid and then twice with ice-cold acetone. The final pellet was dissolved in 500 μl 0.05N NaOH.

The amount of radio-labeled proline incorporated into CDP and NCP was determined according to the method of Peterkofsky and Diegelmann (Peterkofsky, B., and Diegelmann, R., "Use of a mixture of proteinase-free collagenases for the specific assay of radioactive collagen in the presence of other proteins," Biochemistry (1971) 10:988–994). Data were expressed as dpm and were calculated with respect to protein content. Highly purified clostridial collagenase, 158 U/mg protein, was obtained from Calbiochem (San Diego, Calif.). This batch of enzyme was found to be very low in nonspecific proteolytic activity. Less than 5% of the total incorporated radioactivity was released from [$^3$H]-tryptophan-labeled chondrocytes. The protein content of each fraction was determined by a miniaturization of the method of Lowry et al. (Lowry, O. H. et al., "Protein measurement with the folin phenol reagent," J. Biol. Chem. (1951) 193:265–275). For most experiments, CDP and NCP were only measured in the cell layer, not the media, because more than 80% of the total CDP was incorporated into the cell layer. This assay did not take into account any degradation that may have occurred.

Proteoglycan synthesis was assessed by measuring [$^{35}$S]-sulfate incorporation according to the method of Regis et al. (Regis, J. O. et al., "Effects of transforming growth factor β on matrix synthesis by chick growth plate chondrocytes," Endocrinology (1988) 122:2953–2961). In prior studies, we have found that the amount of radiolabeled proteoglycan released by growth zone and resting zone chondrocytes into the medium was less than 15% of the total radiolabeled proteoglycan (media and cell layer) synthesized (Nasatzky, E., et al., "Sex dependent effects of 17β estradiol on chondrocyte differentiation in culture," J. Cell. Phys. (1993) 156:359–367). Because of this, we only examined the effects of hormone treatment on $^{35}$SO$_4$ incorporation in the cell layer. This assay does not measure any degradation that may occur during the culture.

For assay, fourth passage resting zone chondrocytes were grown to confluence in 24-well culture plates (Corning, Corning, N.Y.) with media containing 10% FBS, antibiotics, and 50 μg/ml ascorbic acid. Twenty-four hours prior to harvest, fresh media containing vehicle alone or vitamin D was added to the cells. Four hours prior to harvest, 50μDMEM containing 18 μCi/ml $^{35}$SO$_4$ and 0.814 mM carrier sulfate was added to each culture. At harvest, the conditioned media were removed and the cell layers (cells and matrix) collected in two 0.25 ml portions of 0.25M NaOH. The protein content was determined by the method of Lowry et al., (Lowry, O. H. et al., "Protein measurement with the folin phenol reagent," J. Biol. Chem. (1951) 193:265–275). The total volume was adjusted to 0.75 ml by the addition of 0.15M NaCl and the sample dialyzed in a 12,000–14,000 molecular weight cut off membrane against buffer containing 0.15M NaCl, 20 mM Na$_2$SO$_4$, and 20mM Na$_2$HPO$_4$, pH 7.4, at 4° C. The dialysis solution was changed until the radioactivity in the dialysate reached background. The amount of $^{35}$SO$_4$ incorporated was determined by liquid scintillation spectrometry and calculated as DPM/mg protein in the cell layer. This protocol was also used for assessing the change in phenotype induced by 24,25-(OH)$_2$D$_3$-pretreatment of resting zone chondrocytes.

The data generated were from one experiment that was repeated three or more times with comparable results. For any given experiment, each data point represents the mean ± SEM for six individual cultures. Treatment/control ratios were derived from five or more independent experiments, with controls having a ratio of 1.0.

The data were analyzed by analysis of variance, and statistical significance determined by comparing each data point to the control (containing ethanol vehicle) using Bonferroni's modification of the t-test. Treatment/control ratios were compared using the Wilcoxon matched pair rank sum test. $P<0.05$ was considered significant.

Addition of $10^{-8}$ to $10^{-10}$M $1,25\text{-}(OH)_2D_3$ to resting zone cells pretreated with $10^{-7}$M $24,25\text{-}(OH)_2D_3$ rods for 24 or 48 hours caused a dose-dependent inhibition in $[^3H]$-thymidine incorporation. The inhibitory effect was also observed in chondrocytes pretreated for up to 120 hours with $24,25\text{-}(OH)_2D_3$. Resting zone cells pretreated with vehicle alone and challenged with $1,25\text{-}(OH)_2D_3$ incorporated $[^3H]$-thymidine at levels comparable to cells that were pretreated with $24,25\text{-}(OH)_2D_3$ followed by treatment with $10^{-8}$M $1,25\text{-}(OH)_2D_3$.

Addition of $1,25\text{-}(OH)_2D_3$ had no effect on alkaline phosphatase specific activity of resting zone chondrocytes pretreated with $10^{-7}$M $24,25\text{-}(OH)_2D_3$ in for 24 hours. Enzyme activity in these cultures was comparable to that of cells incubated with $10^{-8}$M $1,25\text{-}(OH)_2D_3$ with no $24,25\text{-}(OH)_2D_3$ pretreatment. However, when resting zone cells were pretreated with $24,25\text{-}(OH)_2D_3$ for 48 hours, there was a dose-dependent increase in alkaline phosphatase specific activity which was significant at concentrations of $10^{-9}$M and $10^{-8}$M $1,25\text{-}(OH)_2D_3$.

The effect of $24,25\text{-}(OH)_2D_3$ pretreatment was observed by 36 hours. Pretreatment with $24,25\text{-}(OH)_2D_3$ enhanced the stimulation of alkaline phosphatase specific activity by $1,25\text{-}(OH)_2D_3$ in a time-dependent manner. Maximum effects were observed in cultures incubated for 72 hours with $24,25\text{-}(OH)_2D_3$, and the effect was maintained in cells pre-cultured for 120 hours. In contrast, resting zone cells pretreated with vehicle alone failed to exhibit $1,25\text{-}(OH)_2D_3$-dependent increases in enzyme activity. Alkaline phosphatase activity in these cultures was comparable to that seen in cultures pretreated with $24,25\text{-}(OH)_2D_3$, but challenged with vehicle alone. Pretreatment of resting zone chondrocytes with $1,25\text{-}(OH)_2D_3$ had no effect on the responsiveness of cells to $1,25\text{-}(OH)_2D_3$.

Xiphoid cells responded to pretreatment with $24,25\text{-}(OH)_2D_3$ in a manner distinct from the resting zone cells. Cultures preincubated with vehicle alone and challenged with vehicle exhibited comparable enzyme activity, regardless of the length of pretreatment. In cultures pretreated with vehicle alone or with $24,25\text{-}(OH)_2D_3$ for 24 hours, $1,25\text{-}(OH)_2D_3$ inhibited alkaline phosphatase specific activity in a dose-dependent manner. The effect of $1,25\text{-}(OH)_2D_3$ was not seen in xiphoid cells preincubated with $24,25\text{-}(OH)_2D_3$ for 36, 48 or 72 hours.

$[^3H]$-Uridine incorporation was unaffected by any of the treatment regimens used.

Following a 24-hour pretreatment with $24,25\text{-}(OH)_2D_3$, resting zone chondrocytes exhibited a dose-dependent decrease in synthesis of collagenase-digestible protein when exposed to $1,25\text{-}(OH)_2D_3$. At the highest concentration of $1,25\text{-}(OH)_2D_3$, CDP synthesis was comparable to that seen in chondrocytes pretreated with vehicle alone. NCP synthesis was unaffected by any of the treatment protocols. The percent collagen production calculated from the CDP/NCP ratio also demonstrated a dose-dependent inhibition when the pretreated chondrocytes were exposed to $1,25\text{-}(OH)_2D_3$. These observations were consistent among experiments.

Following a 48-hour exposure to $24,25\text{-}(OH)_2D_3$, $1,25\text{-}(OH)_2D_3$ stimulated CDP synthesis, with a maximum increase at $10^{-9}$M. A corresponding effect was observed in percent collagen production. When resting zone chondrocytes were pretreated with vehicle alone and then challenged with $1,25\text{-}(OH)_2D_3$, CDP synthesis and percent collagen production were decreased in comparison to cultures pretreated with $24,25\text{-}(OH)_2D_3$ and challenged with vehicle only. These observations were consistent among experiments. As found in the 24 hour pre-treatment group above, NCP synthesis was unaffected by 48 hours of pretreatment as well.

The effect of $24,25\text{-}(OH)_2D_3$ pretreatment on CDP production was time-dependent. In cultures pre-incubated with $24,25\text{-}(OH)_2D_3$ but challenged with vehicle alone, CDP production was unchanged, regardless of the length of pretreatment. When $24,25\text{-}(OH)_2D_3$ pretreated cells were subsequently incubated with $1,25\text{-}(OH)_2D_3$, CDP production was decreased in cultures exposed for 24 hours, but by 36 hours of exposure, there was a marked increase in CDP synthesis. The effect of pretreatment was maximal at 48 hours and was sustained in cultures pretreated for 120 hours. In contrast, in cultures preincubated with vehicle alone and challenged with $1,25\text{-}(OH)_2D_3$, CDP production remained decreased, regardless of the length of pre-incubation. NCP was unaffected under all treatment protocols. Consequently, the effects of treatment on percent collagen production mirrored those on CDP production.

The effect of vitamin D metabolites on sulfate incorporation by growth zone and resting zone chondrocytes has not been reported, so before examining the effect of pretreatment with $24,25\text{-}(OH)_2D_3$, we characterized the baseline effects of both vitamin D metabolites on the two cells.

$1,25\text{-}(OH)_2D_3$ stimulated $^{35}SO_4$ incorporation by growth zone chondrocytes. The effect was significant at $10^{-9}$M to $10^{-8}$M. No effect was observed when $1,25\text{-}(OH)_2D_3$ was added to resting zone cells. $24,25\text{-}(OH)_2D_3$ had no effect on $^{35}SO_4$ incorporation by growth zone cells. In resting zone cells incubated with $24,25\text{-}(OH)_2D_3$, there was a dose-dependent increase in proteoglycan production at $10^{-9}$M to $10^{-8}$M, with a peak at $10^{-8}$M.

The addition of $1,25\text{-}(OH)_2D_3$ to resting zone cells pretreated for 24 hours with $24,25\text{-}(OH)_2D_3$ produced no effect on sulfate incorporation. A similar level of $^{35}SO_4$ incorporation was found in cultures pre-incubated with vehicle and challenged with $1,25\text{-}OH)_2D_3$. However, if resting zone cells were pretreated with $24,25\text{-}(OH)_2D_3$ for 48 hours, and then incubated with $1,25\text{-}(OH)_2D_3$, a dose-dependent increase in $SO_4$ incorporation was observed. $1,25\text{-}(OH)_2D_3$-dependent increases in $^{35}SO_4$ incorporation were seen only in cultures pretreated for a minimum of 48 hours.

The results of the present study provide evidence that fourth passage chondrocytes derived from the resting zone of rat costochondral cartilage exhibit a distinct phenotype compared with cells derived from the growth zone. Incorporation of $[^{35}S]$-sulfate by these cultures, presumably into proteoglycan, was dependent on both the state of cell maturation and vitamin D metabolite used. $1,25\text{-}(OH)_2D_3$ affected cells derived from the growth zone, whereas $24,25\text{-}(OH)_2D_3$ affected cells derived from the resting zone.

Resting zone chondrocytes appear to be specific target cells for $24,25\text{-}(OH)_2D_3$. While previous studies have shown that cell metabolism is affected by $24,25\text{-}(OH)_2D_3$, this is the first study to provide a definitive demonstration that this hormone induces differentiation. Resting zone chondrocytes pre-treated with $24,25\text{-}(OH)_2D_3$ not only acquired responsiveness to $1,25\text{-}(OH)_2D_3$, a growth zone chondrocyte trait, but exhibited a phenotype consistent with authentic growth zone cells.

The ability of 24,25-$(OH)_2D_3$ to induce this effect was not due to a nonspecific phenomenon during pre-incubation of the cells. Neither pre-incubation with vehicle alone for up to 120 hours, nor pre-incubation with 1,25-$(OH)_2D_3$ induced differentiation of these cells. In fact, the response of the cells pretreated with vehicle alone or with 1,25-$(OH)_2D_3$ to challenge with 1,25-$(OH)_2D_3$ was entirely consistent with their being resting zone chondrocytes. Alkaline phosphatase specific activity and sulfate incorporation were unchanged, but collagen production was inhibited. These experiments also confirmed our previous observation that exposure to the ethanol vehicle alone had no measurable effect on these cells.

Resting zone chondrocytes required a minimum of 36–48 hours exposure to 24,25-$(OH)_2D_3$ before responsiveness to 1,25-$(OH)_2D_3$ was detectable. For example, there was no difference in [$^3$H]-proline incorporation into collagenase-digestible protein in chondrocytes treated with 1,25-$(OH)_2D_3$ for 24 hours, whether or not they were pretreated with 24,25-$(OH)_2D_3$. In both instances, CDP production was decreased by treatment with 1,25-$(OH)_2D_3$. In contrast, after 48 hours of pretreatment with 24,25-$(OH)_2D_3$, CDP production was significantly higher than in the non-24,25-$(OH)_2D_3$ pretreated cells and was further stimulated by 1,25-$(OH)_2D_3$.

The data suggest that 24,25-$(OH)_2D_3$ initiates a differentiation cascade. This hypothesis is supported by the observation that maximal response to 1,25-$(OH)_2D_3$ is not achieved until the resting zone cells have been pretreated with 24,25-$(OH)_2D_3$ for 72 hours. Further, this was the case for all parameters examined.

Although 24,25-$(OH)_2D_3$ has the ability to induce differentiation of resting zone cells in vitro, it probably promotes its effect in concert with other local factors and hormones. When fetal mouse bones are exposed to 24,25-$(OH)_2D_3$, the effects of the hormone on growth and development are observed only in serum-containing media (Schwartz, Z. et al., "A direct effect of 24,25-$(OH)_2D_3$ and 1,25-$(OH)_2D_3$ on the modeling of fetal mice long bones in vitro," J. Bone Min. Res. (1989) 4:157–163). Effects of another steroid hormone, 17β-estradiol, on the chondrocytes were also dependent on the presence of FBS in the medium (Nasatzky, E. et al., "Sex dependent effects of 17β estradiol on chondrocyte differentiation in culture," J. Cell. Phys. (1993) 156:359–367). The requirement for serum may be due in part to the presence of binding proteins needed for proper presentation of the hormone to the cell. In addition, growth factors in the serum may play a role. For example, as discussed above TGFβ has a synergistic effect with 24,25-$(OH)_2D_3$ on resting zone chondrocytes; the complex regulation of chondrocyte differentiation by other factors and hormones has been shown by numerous investigators.

The regulation of chondrocyte differentiation by 24,25-$(OH)_2D_3$ involves at least two major steps. As shown by this study, it causes the less mature resting zone chondrocyte to advance in the endochondral differentiation cascade and develop a growth zone chondrocyte phenotype. 24,25-$(OH)_2D_3$ also regulates production of vitamin D metabolites by the chondrocytes (Schwartz, Z. et al., "Production of 1,25-$(OH)_2D_3$ and 24,25-$(OH)_2D_3$ by growth zone and resting zone chondrocytes is dependent on cell maturation and is regulated by hormones and growth factor," Endocrinology (1992) 130:2495–2504). While it down-regulates production of 24,25-$(OH)_2D_3$ by resting zone cells, it up-regulates production of 1,25-$(OH)_2D_3$ by growth zone cells. Thus, as the resting zone cells acquire a growth zone phenotype, production of 1,25-$(OH)_2D_3$ may be stimulated, regulating the next stage of differentiation in an autocrine manner.

This study also indicates that cells isolated from xiphoid cartilage are distinct from resting zone chondrocytes in their phenotype, although both cell types are derived from proteoglycan-rich cartilaginous tissues. Whereas alkaline phosphatase activity in resting zone cell cultures is unaffected by 1,25-$(OH)_2D_3$, it is inhibited in xiphoid cell cultures. Only after a minimum of 36 hours exposure to 24,25-$(OH)_2D_3$ do these cells become nonresponsive to 1,25-$(OH)_2D_3$, suggesting that they may have acquired a different phenotype, perhaps a resting zone chondrocyte phenotype. This is consistent with the hypothesis that there is a chondrocyte lineage continuum from the noncalcifying hyaline xiphoid cartilage cell through the calcifying chondrocyte, with the time spent in the resting zone maturation state being dependent on anatomic site and physiology of the animal.

While 24,25-$(OH)_2D_3$ appears to promote xiphoid differentiation, 1,25-$(OH)_2D_3$ appears to inhibit this process. In contrast, chondrocytes derived from embryonic chick sternum, also a hyaline type of cartilage, can become hypertrophic in vitro following 12 days of exposure to 1,25-$(OH)_2D_3$ (Schwartz, Z. et al., "Regulation of prostaglandin $E_2$ synthesis by vitamin D metabolites in growth zone and resting zone chondrocyte cultures is dependent on cell maturation," Bone (1992) 13:395–401). It is likely that the differences in the two model systems account for some of the apparent inconsistency in the observations. The length of treatment, species and age of the animal model, and selection criteria of cells for culture all varied. Even with these differences in experimental design, both models support the concept of a chondrogenic differentiation cascade.

The results of our study provide further evidence of the importance of 24,25-$(OH)_2D_3$ in chondrocyte differentiation and confirm previous observations, and those of other laboratories, that 24,25-$(OH)_2D_3$ can regulate cartilage cell proliferation and matrix production and growth plate maturation. This study demonstrates for the first time that 24,25-$(OH)_2D_3$ specifically targets resting zone cells, inducing their differentiation along the endochondral developmental pathway. Moreover, it shows for the first time that xiphoid cartilage cells are regulated by 24,25-$(OH)_2D_3$ in a manner distinct from resting zone cells. The role of 24,25-$(OH)_2D_3$ in resting zone cell differentiation appears to be specific to this metabolite, since pretreatment with 1,25-$(OH)_2D_3$ was not effective.

Example 4

Isolation of matrix vesicles.

Matrix vesicles, extracellular organelles that are membrane bound and have diameters of approximately 200–450 Angstroms, are isolated from calcifying tissues and have a characteristic alkaline phosphatase specific activity that is greater than 2-fold the activity found in the plasma membranes of the cells which formed the matrix vesicles. Matrix vesicles also tend to be high in phosphatidylserine content.

Matrix vesicles are prepared from cell cultures as follows. At harvest, the conditioned media are decanted and the cells are released by trypsinization (1% in Hank's balanced salt solution). The reaction is stopped with Dulbecco's modified Eagle's medium containing 10% fetal bovine serum. The cells are collected by centrifugation at 500× g for 10 minutes. The supernatant from the trypsin digest is centrifuged for 20 minutes at 13,000×g to pellet a mitochondria/membrane fraction, and the resulting supernatant is centrifuged for one hour at 100,000× g to pellet matrix vesicles. Matrix vesicles are resuspended in 1 ml 0.9% NaCl and stored frozen at −20° to −70° C. until used.

Example 5

Matrix Vesicle Extract.

Matrix vesicle extract is made using the following protocol. Equal volumes of the matrix vesicle suspension (1 mg protein/ml in 0.9% NaCl) are mixed with 0.1M Tris buffer, pH 7.5, containing 4M guanidine HCl, 0.02M $CaCl_2$ and 0.4% Triton X-100. The membrane suspension is briefly mixed for 20–30 seconds with a ground glass homogenizer (Duall #20, Kontes Co., Vineland, N.J.) and then stirred for 2 hours at 4° C. The extract is then centrifuged at 106,000× g for 1 hour and the supernatants dialyzed into metalloproteinase or plasminogen activator assay buffer.

Matrix vesicles prepared in this manner exhibit neutral metalloproteinase activity (specifically, stromelysin), acid metalloproteinase activity, and plasminogen activator. Gelatinase activity may also be present.

Example 6

Method of making matrix vesicles having intercalated REF.

Matrix vesicles isolated as described in Example 4 are incubated with 1,25-$(OH)_2D_3$ as described in Example 1 for activation of latent TGFβ by isolated matrix vesicles to allow intercalation of the 1,25-$(OH)_2D_3$ into the matrix vesicle membranes. The matrix vesicles are then assayed for the presence of 1,25-$(OH)_2D_3$ by means known to the art and a significant amount is found to have been taken up. The treated matrix vesicles are then tested for their ability to activate latent growth factors, TGFβ, insulin-like growth factor, bone morphogenic protein, platelet-derived growth factor, and fibroblast growth factor, i.e, by the method of Example 1. Significant activation is demonstrated in all cases.

The procedure is repeated incubating the additional REFs estrogen and testosterone with the matrix vesicles. Significant growth factor activation is shown.

Example 7

Conversion of latent growth factor to active growth factor.

The procedure of Example 1 for activation of latent TGFβ by isolated matrix vesicles is followed, successively using latent insulin-like growth factor, latent fibroblast growth factor, latent bone morphogenic protein, and latent platelet-derived growth factor in place of latent TGFβ, and assaying for growth factor activity by bioassays known to the art.

Significant conversion of latent to active growth factor is demonstrated in each instance.

The procedure is repeated deleting the step of incubating the matrix vesicles with 1,25-$(OH)_2D_3$, and significant conversion of each latent growth factor to active form is found.

The procedure is repeated, substituting in turn the REFs estrogen and testosterone for the 1,25-$(OH)_2D_3$, and significant conversion of latent growth factor to active form is seen for all growth factors.

The procedure is repeated omitting the step of incubating the matrix vesicles with 1,25-$(OH)_2D_3$ and instead adding the REF to the latent growth factor and incubating with the matrix vesicles as described. This procedure is repeated with estrogen, testosterone and prostaglandin $E_2$. Significant conversion of latent growth factor to active form is seen for all growth factors.

Example 8

Implants for enhancing activation of latent growth factor.

Two-phase biodegradable implants are designed and constructed using 50:50 poly(DL-lactide-co-glycolide)(PLG) with inherent viscosity of 0.71 dl/gm (weight average molecular weight 65 kD). The implant consists of a "bone" phase that abuts against the underlying bone for anchoring and a "cartilage" phase which interfaces with the adjacent layer of articular cartilage. The polymer is solubilized in acetone and precipitated with ethanol. The gummy "bone" composite is placed under 10 m Torr vacuum for six hours and then packed into a Teflon mold under 10 m Torr and 24° C. for 24 hours. The implants are then partially removed and allowed to remain under the same conditions for 24 hours. New polymer is then solubilized in acetone and combined with the appropriate amount of TGFβ. Latent recombinant human TGFβ$_1$ (approximately 4 g) is solubilized in 0.2 ml sterile water, stirred overnight and added to the soft polymer. The appropriate volume of solution to give a total of 500 ng of latent TGFβ is used in the "cartilage" phase only of each implant. The two-phase implants are placed in the mold under 10 m Torr and 4° C. for 24 hours, partially removed, and placed in a lyophilizer under the same conditions for another 24 hours. At the end of the curing period, the implants are completely removed from the mold and stored in the lyophilizer until required for implantation into the host. The curing techniques used for the two phases render the implant porous and the "cartilage" phase softer than the "bone" phase. The two phases are mechanically tested using an automated indenter and modeled using the linear biphasic theory (Mow, V. C. et al., J. Biomech. Eng. (1980) 102:73–84).

At the same time the TGFβ$_1$ is added, 1 ml of a solution of 1,25-$(OH)_2D_3$ as described in Example 1, a sufficient amount to activate said growth factor, is added to the implant.

Cylindrical, 4 mm×6 mm, full-thickness defects are created with a low-speed drill, under saline irrigation, in the central posterior medial condyle of each right knee joint, through a posteromedial approach. Defects are filled with implants containing 500 ng of latent TGFβ, implants without latent growth factor, implants with active rhTGFβ$_1$ or are left empty as controls. The animals are allowed free cage activity for either four or eight weeks, prior to sacrifice. A total of 96 New Zealand male white rabbits are used. The quality of healing is examined at four weeks (48 rabbits) and at eight weeks (48 rabbits) using gross morphology, biomechanics, and histomorphometry. Statistically the results are compared with analysis of variance and multiple comparisons tests.

The repair osteochondral defect and adjacent site are biomechanically tested using an automated indenter under conditions of biphasic creep indentation. The three intrinsic material properties of repair and adjacent cartilage are obtained using a numerical algorithm (Athanasiou et al., Trans. Orth. Res. Soc. (1992) 17(1):172) based on biphasic finite element methods (Spilker et al., J. of Biomech. Eng. (1990) 112:138) and nonlinear optimization techniques. The adjacent site is tested 3 mm anterior to the defect. After biomechanical testing, each osteochondral specimen is sectioned, stained with Alcian blue, and digitized to obtain the geometric parameters needed in the finite element modeling. The Cray supercomputer is used for these analyses. Histologically, each osteochondral specimen is decalcified and stained with hematoxylin and eosin. Sections are analyzed with an image analysis system to measure the percent of trabecular bony repair in each defect.

The group having the implant with latent TGFβ shows significant healing after eight weeks, similar to that with active TGFβ, compared to the group having the implant without TGFβ and the unimplanted control group.

This procedure is repeated using the additional latent growth factors, insulin-like growth factor, platelet-derived growth factor, and fibroblast growth factor, with similar results.

The foregoing procedures are repeated successively using estrogen, testosterone, dexamethasone, prostaglandin $E_2$, thyroid, leukotrienes and platelet activating factors instead of 1,25-$(OH)_2D_3$ with comparable results.

The foregoing procedures are repeated without incorporating REF into the implant, but injecting 1 ml of a $10^{-12}$M solution into the wound site at intervals of 24 hours during the eight-week period. Significant healing is shown compared to controls with and without implants.

The procedures are repeated incorporating 1 ml per cc of polymer of a suspension of matrix vesicles into the implant with and without latent growth factors and REFs. Matrix vesicles having REF intercalated into the cell membrane as described in Example 6 are also incorporated into the polymer, with and without latent growth factor. In the implants without latent growth factors and/or REFs, the missing component(s) are injected into the wound site. 1 ml of a 1% solution of latent growth factor is used. The results indicate significant wound healing compared to controls.

The procedures are repeated incorporating 1 ml of a matrix vesicle extract as described in Example 5 with and without latent growth factor. When latent growth factor is not incorporated into the polymer, it is periodically injected into the wound site as described above. Significant healing compared to controls is observed.

Example 9

Cell seeded scaffolding.

Polymeric materials incorporating the full range of combinations of latent growth factors, REFs, matrix vesicles with and without intercalated REFs, and matrix vesicle extracts described above are prepared as described in Example 8, except that rather than forming cylindrical implants with such polymers, three-dimensional scaffolds as described in U.S. Pat. No. 5,160,490, incorporated herein by reference, are prepared. The scaffolds are seeded with osteoblasts, chondrocytes or tendon cells, and cultured as described in said patent. In each instance where the necessary REF, latent growth factor, or matrix vesicle material required for activation of latent growth factor is not incorporated into the polymer, it is added to the culture medium. Significantly, enhanced growth and differentiation of cells is shown.

This invention has been described with reference to preferred embodiments; however, it will be apparent to those skilled in the art that additional equivalent procedures and compositions may be substituted in the practice of this invention for those disclosed herein within the scope and spirit of applicants contribution to the art. The appended claims are to be interpreted to include all such modifications and equivalents.

We claim:

1. An in vitro method for stimulating activation of isolated latent Transforming Growth Factor-$\beta$ (TGF$\beta$) comprising adding to a medium comprising said isolated latent growth factor an amount of isolated matrix vesicles or isolated vesicle extract sufficient to stimulate activation of said isolated growth factor.

2. The method of claim 1 comprising adding to said medium isolated matrix vesicles.

3. The method of claim 2 comprising adding to said medium 1,25-dihydroxy-vitamin D (1,25-$(OH)_2D_3$) in an amount sufficient to stimulate said isolated matrix vesicles to produce latent TGF$\beta$ activating factor.

4. The method of claim 3 wherein said 1,25-$(OH)_2D_3$ is intercalated into the vesicle membranes.

5. The method of claim 2 comprising adding to said medium isolated matrix vesicle extract.

6. A composition consisting essentially of (a) isolated latent TGF$\beta$, and (b) isolated matrix vesicles or isolated matrix vesicle extract in an amount sufficient to stimulate activation of said isolated latent TGF$\beta$.

7. The composition of claim 6 also containing 1,25-$(OH)_2D_3$.

8. A biodegradable polymeric implant material comprising the composition of claim 6.

9. A biodegradable polymeric implant material comprising the composition of claim 7.

* * * * *